United States Patent
Ouyang et al.

(10) Patent No.: US 12,011,710 B1
(45) Date of Patent: Jun. 18, 2024

(54) TETRAMETALLIC BULK HYDROPROCESSING CATALYSTS

(71) Applicant: Chevron U.S.A. Inc., San Ramon, CA (US)

(72) Inventors: Xiaoying Ouyang, El Cerrito, CA (US); Viorel Duma, Hercules, CA (US); Alexander Kuperman, Orinda, CA (US); Ibrahim Uckung, Richmond, CA (US); Theodorus Ludovicus Michael Maesen, Moraga, CA (US); Axel Brait, San Rafael, CA (US); Charles Wilson, San Francisco, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 18/344,380

(22) Filed: Jun. 29, 2023

Related U.S. Application Data

(62) Division of application No. 17/190,611, filed on Mar. 3, 2021, now Pat. No. 11,731,112.

(Continued)

(51) Int. Cl.
  B01J 37/20 (2006.01)
  B01J 23/89 (2006.01)
  (Continued)

(52) U.S. Cl.
  CPC ........... B01J 23/8993 (2013.01); B01J 35/31 (2024.01); B01J 35/615 (2024.01); B01J 35/633 (2024.01); B01J 37/0045 (2013.01); B01J 37/031 (2013.01); B01J 37/04 (2013.01); B01J 37/08 (2013.01); B01J 37/20 (2013.01); C07C 5/10 (2013.01); C10G 45/00 (2013.01); C10G 47/00 (2013.01); C10G 49/00 (2013.01); C10G 2300/1055 (2013.01); C10G 2300/1074 (2013.01); C10G 2300/4006 (2013.01);
(Continued)

(58) Field of Classification Search
  CPC ...... B01J 23/8993; B01J 35/31; B01J 35/615; B01J 35/633; B01J 37/0045; B01J 37/031; B01J 37/04; B01J 37/08; B01J 37/20; C07C 5/10; C10G 45/00; C10G 47/00; C10G 49/00; C10G 2300/1055; C10G 2300/1074; C10G 2300/4006; C10G 2300/4012; C10G 2300/4018; C10G 2300/42; C10G 2300/70
  See application file for complete search history.

(56) References Cited

U.S. PATENT DOCUMENTS 4,206,036 A  6/1980  Takeuchi et al.
4,609,769 A  9/1986  Kukes et al.
(Continued)

FOREIGN PATENT DOCUMENTS

EP  1 599 285 B1  6/2017

OTHER PUBLICATIONS

PCT International Search Report, International Appl. No. PCT/IB2021/051748, mailed Jun. 11, 2021.

*Primary Examiner* — In Suk C Bullock
*Assistant Examiner* — Jason Y Chong
(74) *Attorney, Agent, or Firm* — E. Joseph Gess; Melissa M. Hayworth; Terrence M. Flaherty

(57) ABSTRACT

Bulk catalysts comprised of nickel, molybdenum, tungsten and titanium and methods for synthesizing bulk catalysts are provided. The catalysts are useful for hydroprocessing, particularly hydrodesulfurization and hydrodenitrogenation, of hydrocarbon feedstocks.

40 Claims, 5 Drawing Sheets

Related U.S. Application Data

(60) Provisional application No. 63/019,479, filed on May 4, 2020.

(51) Int. Cl.
*B01J 35/31* (2024.01)
*B01J 35/61* (2024.01)
*B01J 35/63* (2024.01)
*B01J 37/00* (2006.01)
*B01J 37/03* (2006.01)
*B01J 37/04* (2006.01)
*B01J 37/08* (2006.01)
*C07C 5/10* (2006.01)
*C10G 45/00* (2006.01)
*C10G 47/00* (2006.01)
*C10G 49/00* (2006.01)

(52) U.S. Cl.
CPC ........... *C10G 2300/4012* (2013.01); *C10G 2300/4018* (2013.01); *C10G 2300/42* (2013.01); *C10G 2300/70* (2013.01)

(56) References Cited

U.S. PATENT DOCUMENTS

| | | |
|---|---|---|
| 7,544,285 B2 | 6/2009 | Domokos et al. |
| 7,557,062 B2 | 7/2009 | Domokos et al. |
| 7,749,937 B2 | 7/2010 | Domokos et al. |
| 7,803,735 B2 | 9/2010 | Maesen et al. |
| 7,807,599 B2 | 10/2010 | Maesen et al. |
| 7,816,298 B2 | 10/2010 | Maesen et al. |
| 7,838,696 B2 | 11/2010 | Maesen et al. |
| 7,910,761 B2 | 3/2011 | Maesen et al. |
| 8,088,706 B2 | 1/2012 | Domokos et al. |
| 8,206,575 B2 | 6/2012 | Maesen et al. |
| 8,664,146 B2 | 3/2014 | Domokos et al. |
| 9,415,384 B2 | 8/2016 | He et al. |
| 9,719,031 B2 | 8/2017 | Bonne et al. |
| 9,776,180 B2 | 10/2017 | Inoue et al. |
| 2003/0153633 A1 | 8/2003 | Geerlings et al. |
| 2009/0107883 A1 | 4/2009 | Maesen et al. |
| 2010/0279855 A1 | 11/2010 | Dykstra et al. |
| 2017/0165656 A1 | 6/2017 | Miller et al. |

TETRAMETALLIC BULK HYDROPROCESSING CATALYSTS

CROSS-REFERENCE TO RELATED APPLICATIONS

This application is a divisional of U.S. patent application Ser. No. 17/190,611, filed Mar. 3, 2021, which claims priority to and the benefit of U.S. Provisional Application Ser. No. 63/019,479, filed May 4, 2020. U.S. patent application Ser. No. 17/190,611 is hereby incorporated by reference in its entirety.

FIELD

This disclosure relates to tetrametallic bulk catalysts for use in hydroprocessing of hydrocarbon feeds, as well as methods for preparing such catalysts.

BACKGROUND

The hydroprocessing of hydrocarbon feedstocks generally encompasses all processes in which a hydrocarbon feedstock is reacted with hydrogen in the presence of a catalyst and under hydroprocessing conditions, typically, at elevated temperature and elevated pressure. Hydroprocessing includes processes such as hydrodesulfurization, hydrodenitrogenation, hydrodeoxygenation, hydrodemetallation, hydrodearomatization, hydrogenation, hydrogenolysis, hydrotreating, hydroisomerization, and hydrocracking.

Hydroprocessing catalysts usually comprise one or more sulfided Group 6 metals with one or more Group 8 to 10 non-noble metals as promoters on a refractory support, such as alumina. Hydroprocessing catalysts that are particularly suitable for hydrodesulfurization, as well as hydrodenitrogenation, generally comprise molybdenum or tungsten sulfide promoted with a metal such as cobalt, nickel, iron, or a combination thereof.

In addition to supported catalysts, hydroprocessing using bulk catalysts (also referred to as "unsupported" catalysts) are also known. Although bulk hydroprocessing catalyst compositions have relatively high catalytic activity relative to conventional supported hydroprocessing catalysts, there exists a continuous need in the art to develop novel bulk catalyst compositions with further improved hydroprocessing activity.

SUMMARY

In a first aspect, there is provided a bulk catalyst precursor comprising: (a) 1 to 60 wt. % of Ni, on a metal oxide basis; (b) 1 to 40 wt. % of Mo, on a metal oxide basis; (c) 5 to 80 wt. % of W, on a metal oxide basis; and (d) 2 to 45 wt. % of Ti, on a metal oxide basis.

In a second aspect, there is provided a sulfided bulk catalyst characterized in that it is the bulk catalyst precursor described herein that has been sulfided.

In a third aspect, there is provided a method for preparing the bulk catalyst precursor described herein, the method comprising: (a) combining in a reaction mixture: (i) a Ni-containing precursor; (ii) a Mo-containing precursor; (iii) a W-containing precursor; (iv) a Ti-containing precursor; (v) optionally, an organic compound-based component; and (vi) a protic liquid; and (b) reacting the mixture under conditions sufficient to cause precipitation of the bulk catalyst precursor; wherein the steps to prepare the bulk catalyst precursor are carried out at a temperature of no more than 200° C.

In a fourth aspect, there is provided a method for preparing the bulk catalyst precursor described herein, the method comprising: (a) combining in a reaction mixture: (i) a Ni-containing precursor; (ii) a Mo-containing precursor; (iii) a W-containing precursor; (iv) optionally, an organic compound-based component; and (v) a protic liquid; and (b) reacting the mixture under conditions sufficient to cause precipitation of an intermediate bulk catalyst precursor; and (c) compositing the intermediate bulk catalyst precursor with a Ti-containing precursor to form the bulk catalyst precursor; wherein the steps to prepare the bulk catalyst precursor are carried out at a temperature of no more than 200° C.

In a fifth aspect, there is provided a process for hydroprocessing a hydrocarbon feedstock, the process comprising contacting the hydrocarbon feedstock with hydrogen in the presence of a bulk catalyst at hydroprocessing conditions to give at least one product, wherein the bulk catalyst is a derived or derivable from a catalyst precursor comprising: (a) 1 to 60 wt. % of Ni, on a metal oxide basis; (b) 1 to 40 wt. % of Mo, on a metal oxide basis; (c) 5 to 80 wt. % of W, on a metal oxide basis; and (d) 2 to 45 wt. % of Ti, on a metal oxide basis.

DETAILED DESCRIPTION

Definitions

The term "bulk", when describing a mixed metal catalyst composition, may be used interchangeably with "unsupported", meaning that the catalyst composition is not of the conventional catalyst form which has a preformed, shaped catalyst support which is then loaded with metals via impregnation or deposition catalyst.

The term "atmospheric pressure" is used herein to describe an earth air pressure wherein no external pressure modifying means is utilized. Generally, unless practiced at extreme earth altitudes, "atmospheric pressure" is about 1 atmosphere (about 14.7 psi or about 101 kPa).

The terms "weight percent," and "wt. %", which can be used interchangeably, indicate the percent by weight of a given component based on the total weight of the composition, unless otherwise specified. That is, unless otherwise specified, all wt. % values are based on the total weight of the composition. It should be understood that the sum of wt. % values for all components in a disclosed composition or formulation are equal to 100.

Bulk Catalysts and Bulk Catalyst Precursors

Tetrametallic bulk catalyst precursor compositions comprising oxides of Ni, Mo, W, and Ti are provided. Prior to use for hydroprocessing, the catalyst precursor can be sulfided which converts metals to metal sulfides. After sulfidation, the composition corresponds to/is defined as a "catalyst" for the purposes of the claims below.

The bulk catalyst and/or corresponding bulk catalyst precursor comprises nickel (Ni), molybdenum (Mo), tungsten (W) and titanium (Ti) metals. The bulk catalyst and/or corresponding bulk catalyst precursor may contain from 1 to 60 wt. % of Ni, such as from 5 to 40 wt. % or from 20 to 60 wt. %, on a metal oxide basis; from 1 to 40 wt. % of Mo, such as from 1 to 25 wt. % or from 3 to 20 wt. %, on a metal oxide basis; from 5 to 80 wt. % of W, such as from 10 to 35 wt. % or from 20 to 75 wt. %, on a metal oxide basis; and from 2 to 45 wt. % of Ti, such as from 5 to 40 wt. %, from 10 to 35 wt. % or 20 to 30 wt. %, on a metal oxide basis. Thus, the bulk catalysts disclosed herein can have the nomenclature Ni—Mo—W—Ti wherein each metal is present in amounts specified above.

Figure 1:
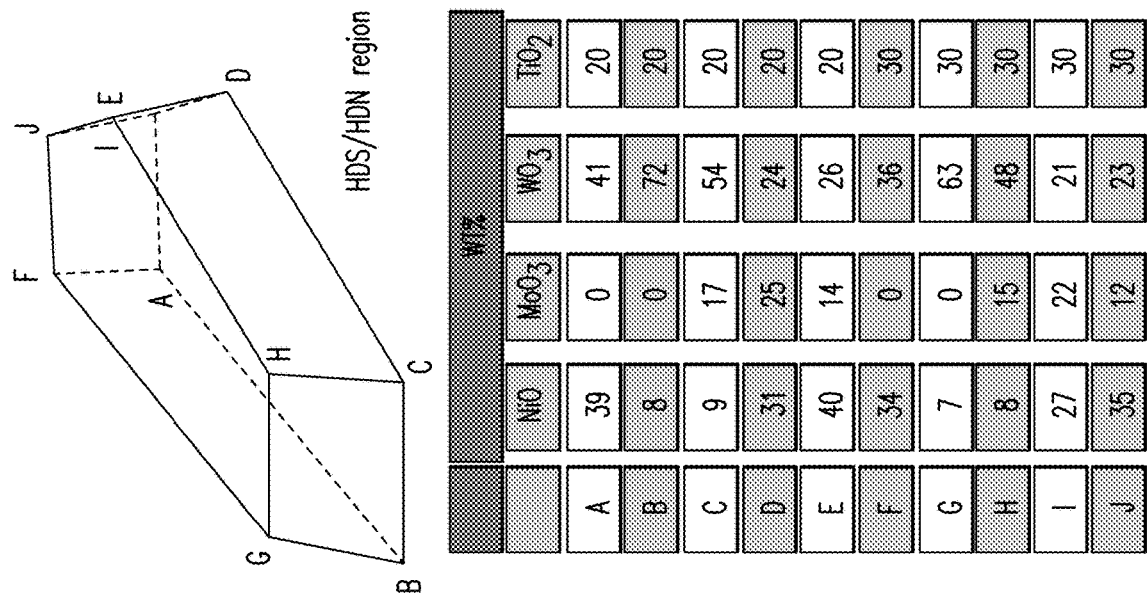
FIG. 1 shows a quaternary phase diagram with the fractional coordinates of the vertices that define the polyhedral Ni—Mo—W—Ti composition space, according to an aspect of the present disclosure.
Figure 1:
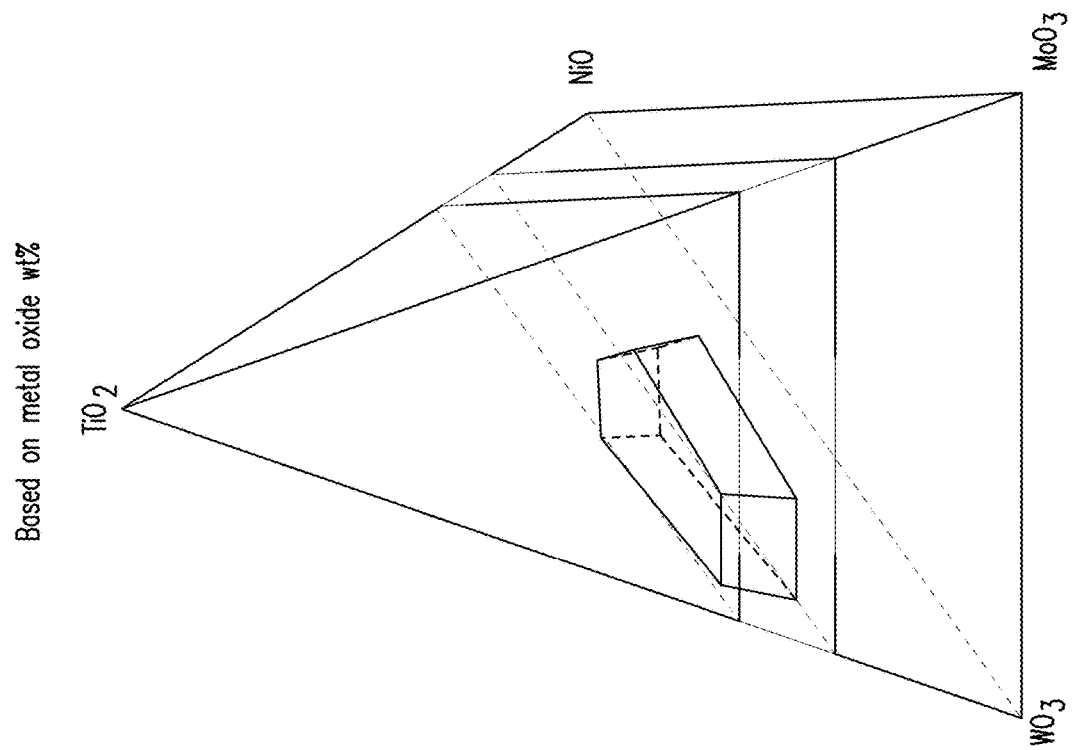

In some aspects, the bulk catalyst and/or corresponding bulk catalyst precursor may be defined by a region of a quaternary phase diagram wherein the region is defined by ten points ABCDEFGHIJ and wherein the ten points, on a metal oxide basis (wt. %), are: A (Ni=39, Mo=0.00, W=41, Ti=20, B (Ni=39, Mo=0.00, W=72, Ti=20); C (Ni=9, Mo=17, W=54, Ti=20), D (Ni=31, Mo=25, W=24, Ti=20), E (Ni=40, Mo=14, W=26, Ti=20), F (Ni=34, Mo=0.00, W=36, Ti=30), G (Ni=7, Mo=0.00, W=63, Ti=30), H (Ni=8, Mo=15, W=48, Ti=30), I (Ni=27, Mo=22, W=21, Ti=30), J (Ni=35, Mo=12, W=23, Ti=30), such as depicted in FIG. 1.

Figure 2:
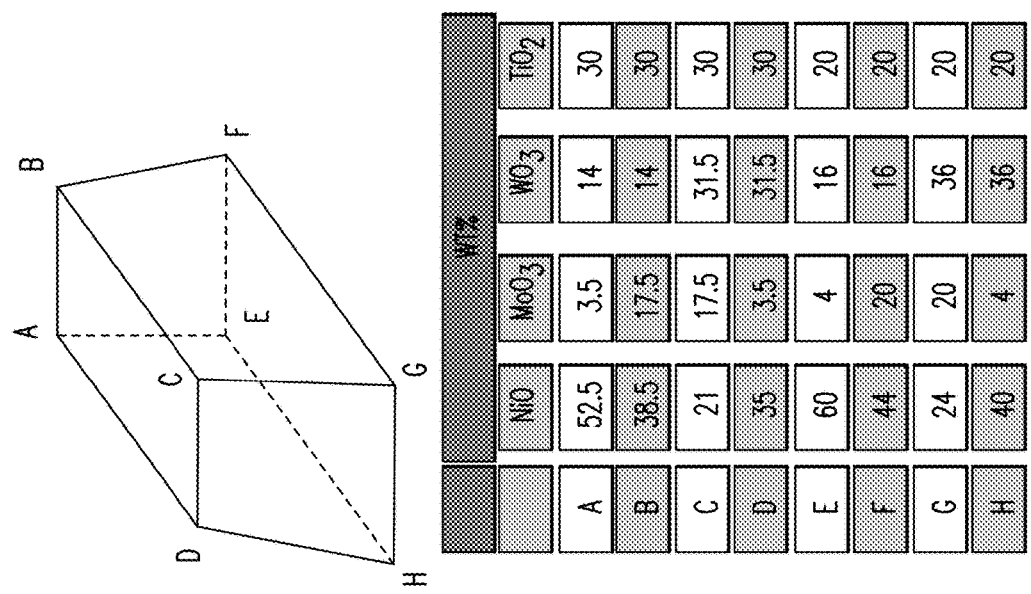
FIG. 2 shows a quaternary phase diagram with the fractional coordinates of the vertices that define the polyhedral Ni—Mo—W—Ti composition space, according to an aspect of the present disclosure.
Figure 2:
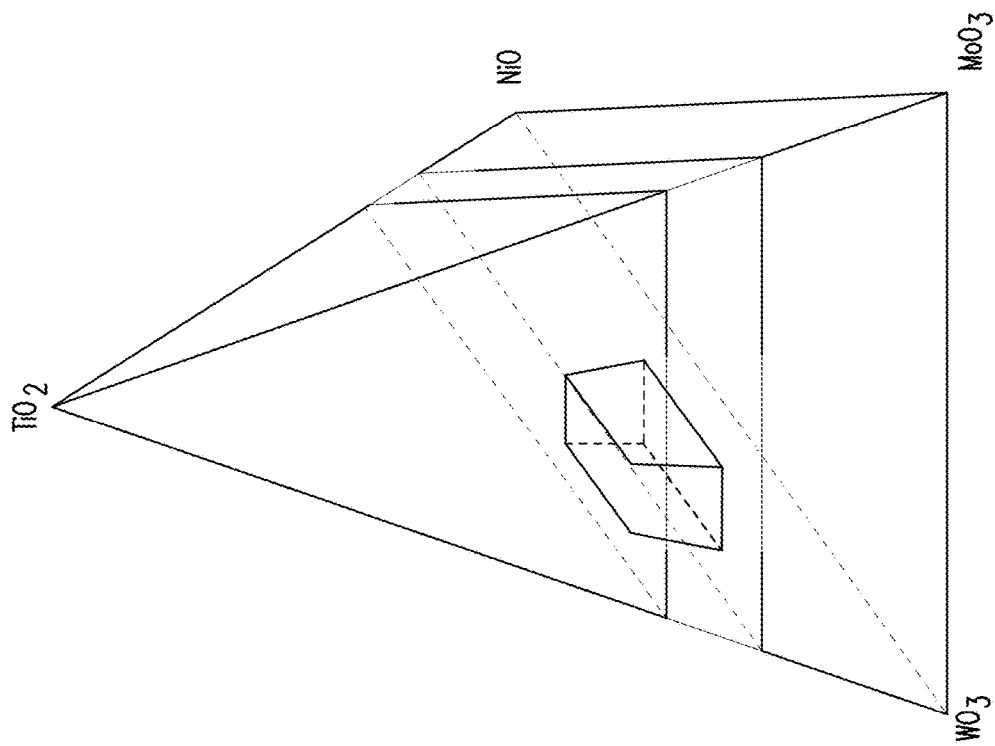

In some aspects, the bulk catalyst and/or corresponding bulk catalyst precursor may be defined by a region of a quaternary phase diagram defined by eight points ABCDEFGH and wherein the eight points, on a metal oxide basis (wt. %), are: A (Ni=52.5, Mo=3.5, W=14, Ti=30), B (Ni=38.5, Mo=17.5, W=14, Ti=30), C (Ni=21, Mo=17.5, W=31.5, Ti=30), D (Ni=35, Mo=3.5, W=31.5, Ti=30), E (Ni=60, Mo=4, W=16, Ti=20), F (Ni=44, Mo=20, W=16, Ti=20), G (Ni=24, Mo=20, W=36, Ti=20), and H (Ni=40, Mo=4, W=36, Ti=20), such as depicted in FIG. 2.

The molar ratios of metals in the bulk catalyst and/or corresponding bulk catalyst precursor can in principle vary between wide ranges. The molar ratio of Ti/(Ni+Mo+W) in the bulk catalyst and/or corresponding bulk catalyst precursor can be in a range of from 10:1 to 1:10 or from 3:1 to 1:3. The molar ratio of Ni/W in the bulk catalyst and/or corresponding bulk catalyst precursor can be in a range of from 10:1 to 1:10. The molar ratio of W/Mo in the bulk catalyst and/or corresponding catalyst precursor can be in a range of 100:1 to 1:100.

The bulk catalyst precursor is a hydroxide and may be characterized as having the following chemical formula:

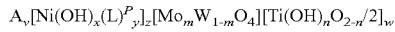

wherein: (i) A is an alkali metal cation, a rare earth metal cation, an ammonium cation, an organic ammonium cation, phosphonium cation, or a combination thereof; (ii) L is an organic compound-based component; and (iii) 0≤y≤−2/p; 0≤x<2; 0≤v<2; 0<z; 0<m<1; 0<n<4; 0.1<w/(z+1)<10.

The bulk catalyst precursor may be comprised of at least 60 wt. % (at least 70 wt. %, at least 80 wt. % or at least 90 wt. %) of oxides of Ni, Mo, W, and Ti prior to sulfiding to form a bulk catalyst. In any aspect, the bulk catalyst and/or corresponding bulk catalyst precursor may contain 40 wt. % or less of a binder material. Binder materials may be added to improve the physical and/or thermal properties of the catalyst.

The bulk catalyst and/or corresponding bulk catalyst precursor may further include an organic compound-based component, which may be based on or derived from at least one organic complexing agent used in the preparation of the bulk catalyst and/or corresponding bulk catalyst precursor. When an organic compound-based component is present, a molar ratio of nickel in the composition to organic compound-based composition can be in a range of from 3:1 to 20:1.

The bulk catalyst and/or corresponding bulk catalyst precursor can have a BET specific surface area of at least 20 m²/g, at least 50 m²/g, at least 75 m²/g, at least 100 m²/g. In any aspect, the self-supported catalyst and/or corresponding self-supported catalyst precursor can have a BET surface area of 250 m²/g or less, 200 m²/g or less, 175 m²/g or less, 150 m²/g or less, or 125 m²/g or less. Each of the above lower limits for the BET specific surface area is explicitly contemplated in conjunction with each of the above upper limits. The term "BET specific surface area" refers to specific surface area as determined from nitrogen adsorption data in accordance with the method of S. Brunauer, P. H. Emmett and E. Teller (*J. Am. Chem. Soc.* 1938, 60, 309-331).

The bulk catalyst and/or corresponding bulk catalyst precursor can have a pore volume of at least 0.02 cm³/g, at least 0.03 cm³/g, at least 0.04 cm³/g, at least 0.05 cm³/g, at least 0.06 cm³/g, at least 0.08 cm³/g, at least 0.09 cm³/g, at least 0.10 cm³/g, at least 0.11 cm³/g, at least 0.12 cm³/g, at least 0.13 cm³/g, at least 0.14 cm³/g, at least 0.15 cm³/g. In any aspect, the self-supported catalyst and/or corresponding self-supported catalyst precursor can have a pore volume of 0.80 cm³/g or less, 0.70 cm³/g or less, 60 cm³/g or less, 50 cm³/g or less 0.45 cm³/g or less, 0.40 cm³/g or less, 0.35 cm³/g or less, 0.30 cm³/g or less. Each of the above lower limits for the pore volume is explicitly contemplated in conjunction with each of the above upper limits. Pore volumes are determined from nitrogen adsorption data in accordance with the procedures described by E. P. Barrett, L. G. Joyner and P. P. Halenda (*J. Am. Chem. Soc.* 1951, 73, 373-380).

The bulk catalyst and/or corresponding bulk catalyst precursor can have a particle density of at least 1.00 g/cm³ (e.g., at least 1.10 g/cm³, at least 1.20 g/cm³, at least 1.30 g/cm³, at least 1.40 g/cm³, at least 1.50 g/cm³, or at least 1.60 g/cm³). In any aspect, the self-supported catalyst and/or corresponding self-supported catalyst precursor can have a particle density of 3.00 g/cm³ or less (e.g., 2.90 g/cm³ or less, 2.80 g/cm³ or less, 2.70 g/cm³ or less, 2.60 g/cm³ or less, 2.50 g/cm³ or less, or 2.40 g/cm³ or less, 2.30 g/cm³ or less, or 2.20 g/cm³ or less). Each of the above lower limits for the particle density is explicitly contemplated in conjunction with each of the above upper limits. Particle density (D) is obtained by applying the formula D=M/V, where M is the weight and V is the volume of the catalyst sample. The volume is determined by measuring volume displacement by submersing the sample into mercury under 28 mm Hg vacuum.

The bulk catalyst and/or corresponding bulk catalyst precursor may be characterized via powder X-ray diffraction as a poorly crystalline material having broad diffraction peaks of low intensity. As used herein, a broad diffraction peak means a peak having a full width at half maximum (FWHM) of more than 1° (in 2-theta scale).

Preparation of the Bulk Catalysts and Catalyst Precursors

The present bulk catalyst precursor is a hydroxide and is prepared by a method wherein the steps prior to sulfiding to form a bulk catalyst are carried out a temperature of no more than 200° C. and wherein the catalyst precursor remains a hydroxide prior to sulfiding to form a bulk catalyst.

In one aspect, the first step in the preparation of the bulk catalyst precursor is a precipitation or co-gelation step, which involves reacting in a reaction mixture a Ni-containing precursor compound in solution and molybdenum and tungsten precursor compounds in solution to obtain a precipitate or co-gel. The precipitation or co-gelation is performed at a temperature and pH at which the nickel precursor and the molybdenum and tungsten precursors precipitate or form a co-gel.

Titanium can be introduced via either an in-situ or an ex-situ route. In the in-situ route, a Ti-containing precursor compound can be added to the reaction mixture to precipitate titanium during co-precipitation or co-gelation of Ni—Mo—W oxides. In the ex-situ route, one or more titanium precursor compounds can be composited with the precipitate or co-gel of Ni—Mo—W oxides.

In any aspect, in-situ addition of titanium can comprise: (a) combining in a reaction mixture: (i) a Ni-containing precursor; (ii) a Mo-containing precursor; (iii) a W-containing precursor; (iv) a Ti-containing precursor; (v) optionally, an organic compound-based component; and (vi) a protic liquid; and (b) reacting the mixture under conditions sufficient to cause precipitation of the bulk catalyst precursor. The reaction mixture may be obtained by: (1) preparing a first mixture comprising a Ni-containing precursor, a protic liquid, and, optionally, an organic compound-based component; (2) preparing a second mixture comprising a Mo-containing precursor, a W-containing precursor, and a protic liquid; (3) adding a Ti-containing precursor to the first mixture, the second mixture, or a combination thereof; (4) heating both the first and second mixtures to a temperature of from 60° C. to 150° C.; (5) combining the first and second mixtures together. After the reaction step, if necessary, the obtained bulk catalyst precursor can be separated from the liquid, e.g., via filtration or spray drying.

In any aspect, ex-situ addition of titanium can comprise: (a) combining in a reaction mixture: (i) a Ni-containing precursor; (ii) a Mo-containing precursor; (iii) a W-containing precursor; (iv) optionally, an organic compound-based component; and (v) a protic liquid; and (b) reacting the mixture under conditions sufficient to cause precipitation of an intermediate bulk catalyst precursor; and (c) compositing the intermediate bulk catalyst precursor with a Ti-containing precursor to form the bulk catalyst precursor. The reaction mixture may be obtained by: (1) preparing a first mixture comprising a Ni-containing precursor, a protic liquid, and, optionally, an organic compound-based component; (2) preparing a second mixture comprising a Mo-containing precursor, a W-containing precursor, and a protic liquid; (3) heating both the first and second mixtures to a temperature of from 60° C. to 150° C.; and (4) combining the first and second mixtures together. After the reaction step, if necessary, the obtained intermediate bulk catalyst can be separated from the liquid, e.g., via filtration or spray drying.

The temperature at which the catalyst precursor is formed can be in a range of from 60° C. to 150° C. If the temperature is below the boiling point of the protic liquid, such as 100° C. in the case of water, the process is generally carried out at atmospheric pressure. The reaction can also be performed under hydrothermal conditions wherein the reaction temperature is above the boiling temperature of the protic liquid. Typically, such conditions give rise to a pressure above atmospheric pressure and then the reaction is preferably performed in an autoclave, preferably under autogenous pressure, that is without applying additional pressure. An autoclave is a device capable of withstanding pressure designed to heat liquids above their boiling temperature. In any aspect, the bulk catalyst precursor formation process is carried out at one or more temperatures either (a) in a range of 50° C. to 100° C. under atmospheric pressure or (b) above 100° C. under autogenous pressure.

The reaction time, both under atmospheric and hydrothermal reaction conditions, is chosen sufficiently long to substantially complete the reaction. The reaction times can be very short (e.g., shorter than 1 hour with highly reactive reactants). Clearly, longer reaction times, perhaps as long as 24 hours, may be required for raw materials with low reactivity. The reaction time can in some circumstances vary inversely with temperature.

Generally, the reaction mixture is kept at its natural pH during the reaction step. The pH can be maintained in a range of 0 to 12 (e.g., 3 to 9, or 5 to 8). The pH can be changed to increase or decrease the rate of precipitation or co-gelation, depending on the desired characteristics of the product.

The metal precursors can be added to the reaction mixture in solution, suspension or a combination thereof. If soluble salts are added as such, they will dissolve in the reaction mixture and subsequently be precipitated or co-gelled.

Representative examples of Mo-containing precursor compounds include molybdenum (di and tri) oxide, molybdic acid, alkali metal molybdates (e.g., sodium molybdate, potassium molybdate), ammonium molybdates (e.g., ammonium molybdate, ammonium dimolybdate, ammonium heptamolybdate), and heteropolymolybdates (e.g., silicomolybdic acid, phosphomolybdic acid).

Representative examples of W-containing precursor compounds include tungsten (di and tri) oxide, tungstic acid, alkali metal tungstates (e.g., sodium tungstate, potassium tungstate, sodium metatungstate, sodium polytungstate), ammonium tungstates (e.g., ammonium tungstate, ammonium metatungstate, ammonium paratungstate), and heteropolytungstates (e.g., silicotungstic acid, phosphotungstic acid).

Representative examples of Ni-containing precursor compounds include nickel acetate, nickel acetylacetonate, nickel bromide, nickel carbonate, nickel hydroxycarbonate, nickel bicarbonate, nickel chloride, nickel nitrate, nickel phosphate, and nickel sulfate.

Any titanium-containing compound suitable for the preparation of a bulk catalyst of the type described herein may be used as a Ti-containing precursor compound. The Ti-containing precursor can comprise a tetravalent titanium ($Ti^{4+}$)-containing compound, a trivalent titanium ($Ti^{3+}$)-containing compound, or a combination thereof.

Representative Ti-containing precursor compounds include $TiO_2$ nanoparticles, colloidal $TiO_2$, fumed $TiO_2$, titanium hydroxide, organotitanium compounds, titanium halides, and water-soluble titanium salts.

The titanium dioxide nanoparticles may be any type of titanium dioxide. The titanium dioxide can have a high content of anatase and/or rutile. For example, the titanium dioxide may comprise at least 50, 55, 60, 65, 70, 75, 80, 85, 90, 95, 98, or even at least 99 percent by weight of anatase and/or rutile. In some embodiments, the titanium dioxide consists essentially of anatase and/or rutile. The titanium dioxide particles preferably have a median particle size (D50) of less than 100 nm (e.g., 3 to 50 nm). The titanium oxide nanoparticles may be introduced in the composition as a sol prepared by dispersion in a dispersant, as a water-or solvent-containing paste, or as a powder. Examples of the dispersant used to prepare a sol include water, alcohols (e.g., methanol, ethanol, isopropanol, n-butanol, isobutanol), and ketones (e.g., methyl ethyl ketone, methyl isobutyl ketone).

Representative organotitanium compounds include titanium alkoxides of the general structure $Ti(OR)_4$ where each R is independently C1 to C4 alkyl and titanium acyl compounds. Representative titanium alkoxides include titanium tetramethoxide, titanium tetraethoxide, titanium tetrapropoxide, titanium tetraisopropoxide, titanium tetra-n-butoxide and titanium tetra-tert-butoxide. Representative titanium acyl compounds include titanium acetylacetonate, titanium oxyacetylacetonate, and titanium acetate. Other representative organotitanium compounds include those characterized by the general formula $Ti(OR')_2(acac)_2$ wherein each R' is independently C1 to C4 alkyl and "acac" is acetylacetonate.

Titanium halides represented by the formula $TiX_4$ or $TiX_3$, where X is chloro, bromo, iodo or fluoro, or mixtures thereof, may be used as titanium precursors. In an aspect, the titanium halide is titanium tetrachloride, titanium tetrabromide, or a combination thereof.

The present disclosure also contemplates the use of organotitanium halides such as chlorotitanium triisopropoxide [$Ti(O-i-Pr)_3Cl$] and the like as Ti-containing precursor compounds.

Representative water-soluble titanium salts include titanium nitrate and titanium sulfate.

The organic compound-based component can be an organic compound suitable for forming metal-ligand complexes in solution. The organic compound-based component may be selected from an organic acid or salt thereof, a sugar, a sugar alcohol, or a combination thereof.

Representative organic acids include glyoxylic acid, pyruvic acid, lactic acid, malonic acid, oxaloacetic acid, malic acid, fumaric acid, maleic acid, tartaric acid, gluconic acid, citric acid, oxamic acid, serine, aspartic acid, glutamic acid, iminodiacetic acid, ethylenediaminetetraacetic acid, and the like.

Representative sugars include fructose, glucose, galactose, mannose, sucrose, lactose, maltose, and the like, and derivatives thereof.

Representative sugar alcohols include erythritol, xylitol, mannitol, sorbitol, and the like, and derivatives thereof.

The protic liquid can be any protic liquid which does not interfere with the reactions of the metal compounds. Examples include water, carboxylic acids, and alcohols (e.g., methanol, ethanol, ethylene glycol). The protic liquid can be water alone or a mixture of water and an alcohol.

Additional Processing

The bulk catalyst precursor may be subjected to one or more of the following process steps before being used in hydroprocessing processes: (i) compositing with a material selected from the group of binder materials, conventional hydroprocessing catalysts, cracking compounds, or mixtures thereof; (ii) spray-drying, (flash) drying, milling, kneading, slurry-mixing, dry or wet mixing, or combinations thereof; (iii) shaping; (iv) drying and/or thermally treating; and (v) sulfiding. The listing of these process steps as (i) to (v) is for convenience only; it is not a statement that these processes are constrained to be performed in this order. These process steps will be explained in more detail below.

Additional Process Step (i)—Compositing with Further Materials

If so desired, an additional material selected from the group of binder materials, conventional hydroprocessing catalysts, cracking compounds, or mixtures thereof can be added during the above-described preparation of the bulk catalyst precursor or the bulk catalyst precursor after its preparation. Preferably, the material is added subsequent to the preparation of the bulk catalyst precursor and prior to spray-drying or any alternative technique, or, if spray-drying or the alternative techniques are not applied, prior to shaping. Optionally, the bulk metal precursor prepared as described above can be subjected to a solid-liquid separation before being composited with the material. After solid-liquid separation, optionally, a washing step can be included. Further, it is possible to thermally treat the bulk catalyst particles after an optional solid-liquid separation and drying step and prior to its being composited with the material.

In all the above-described process alternatives, the phrase "compositing the bulk catalyst precursor with a material" means that the material is added to the bulk metal particles or vice versa and the resulting composition is mixed. Mixing is preferably done in the presence of a liquid ("wet mixing"). This improves the mechanical strength of the final bulk catalyst composition.

Compositing the bulk catalyst precursor with the additional material and/or incorporating the material during the preparation of the catalyst precursor leads to bulk catalyst of particularly high mechanical strength, in particular if the median particle size of the bulk metal particles is in the range of at least 0.5 µm (e.g., at least 1 µm, at least about 2 µm) but not more than 5000 µm (e.g., not more than 1000 µm, not more than 500 µm, not more than 150 µm). The median particle diameter of the catalyst precursor can be in a range of 1 to 150 µm (e.g., 2 to 150 µm).

The compositing of the bulk metal particles with the material results in bulk metal particles embedded in this material or vice versa. Normally, the morphology of the bulk metal particles is essentially maintained in the resulting bulk catalyst composition.

The binder materials to be applied may be any materials conventionally applied as binders in hydroprocessing catalysts. Examples are silica, silica-alumina (e.g., conventional silica-alumina, silica-coated alumina and alumina-coated silica), alumina (e.g., boehmite, pseudoboehmite, or gibbsite), titania, titania-coated alumina, zirconia, hydrotalcite, or mixtures thereof. Preferred binders are silica, silica-alumina, alumina, titania, titania-coated alumina, zirconia, bentonite, or mixtures thereof. These binders may be applied as such or after peptization.

If alumina is used as binder, the surface area of the alumina can be in a range of 50 to 600 $m^2/g$ (e.g., 100 to 450 $m^2/g$), as measured by the BET method. The pore volume of the alumina can be in a range of 0.1 to 1.5 $cm^3/g$, as measured by nitrogen adsorption.

Generally, the binder material to be added has less catalytic activity than the bulk metal particles or no catalytic activity at all. Binder amounts from 0 to 40 wt. % of the total composition can be suitable, depending on the envisaged catalytic application. However, to take advantage of the resulting high activity of the bulk metal particles of the present disclosure, the binder amounts to be added generally are in a range of 0.1 to 30 wt. % (e.g., 1 to 20 wt. %, 3 to 20 wt. %, or 4 to 12 wt. %) of the total composition.

Additional Process Step (ii)—Spray-Drying, (Flash) Drying, Milling, Kneading, Slurry Mixing, Dry or Wet Mixing The bulk catalyst precursor optionally comprising any of the above (further) materials can be subjected to spray-drying, (flash) drying, milling, kneading, slurry-mixing, dry or wet mixing, or combinations thereof, with a combination of wet mixing and kneading or slurry mixing and spray-drying being preferred.

These techniques can be applied either before or after any of the above (further) materials are added (if at all), after solid-liquid separation, before or after a thermal treatment, and subsequent to re-wetting.

Preferably, the catalyst precursor is both composited with any of the above materials and subjected to any of the above techniques. It is believed that by applying any of the above-described techniques of spray-drying, (flash) drying, milling, kneading, slurry-mixing, dry or wet mixing, or combinations thereof, the degree of mixing between the catalyst precursor particles and any of the above materials is improved. This applies to cases where the material is added before as well as after the application of any of the above-described methods. However, it is generally preferred to add the material prior to step (ii). If the material is added subsequent to step (ii), the resulting composition can be thoroughly mixed by any conventional technique prior to any further process steps such as shaping. An advantage of spray-drying is that no waste-water streams are obtained when this technique is applied.

Spray-drying can be carried out at an outlet temperature in the range of 100° to 200° C. (e.g., 120° to 180° C.).

Dry mixing means mixing the catalyst precursor particles in the dry state with any of the above materials in the dry state. Wet mixing generally comprises mixing the wet filter cake comprising the catalyst precursor particles and optionally any of the above materials as powders or wet filter cake to form a homogenous paste thereof.

Additional Process Step (iii)—Shaping

If so desired, the bulk catalyst precursor optionally comprising any of the above (further) materials may be shaped optionally after step (ii) having been applied. Shaping comprises extrusion, pelletizing, beading and/or spray-drying. It is noted that if the bulk catalyst composition is to be applied in slurry-type reactors, fluidized beds, moving beds, or expanded beds, generally spray-drying or beading is applied. For fixed-bed or ebullating bed applications, generally the bulk catalyst composition is extruded, pelletized and/or beaded. In the latter case, at any stage prior to or during the shaping step, any additives which are conventionally used to facilitate shaping can be added. These additives may comprise aluminum stearate, surfactants, graphite, starch, methyl cellulose, bentonite, polyethylene glycols, polyethylene oxides, or mixtures thereof. Further, when alumina is used as binder, it may be desirable to add acids such as nitric acid prior to the shaping step to peptize the alumina and to increase the mechanical strength of the extrudates.

If the shaping comprises extrusion, beading and/or spray-drying, it is preferred that the shaping step is carried out in the presence of a liquid, such as water. For extrusion and/or beading, the amount of liquid in the shaping mixture, expressed as loss-on-ignition, can be in a range of 20% to 80%.

Additional Process Step (iv)—Drying and/or Thermally Treating

After an optional drying step, preferably above 100° C., the resulting shaped bulk catalyst composition may be thermally treated, if desired. A thermal treatment, however, is not essential to the process of this disclosure. A "thermal treatment" according to the present disclosure refers to a treatment performed at a temperature of from 100° C. to 200° C. for a time varying from 0.5 to 48 hours in an inert gas such as nitrogen, or in an oxygen-containing gas, such as air or pure oxygen. The thermal treatment can be carried out in the presence of water steam.

In all the above process steps the amount of liquid must be controlled. Where, prior to subjecting the bulk catalyst composition to spray-drying, the amount of liquid is too low, additional liquid must be added. Conversely where, prior to extrusion of the bulk catalyst composition, the amount of liquid is too high, the amount of liquid must be reduced using solid-liquid separation techniques such as filtration, decantation, or evaporation and, if necessary, the resulting material can be dried and subsequently re-wetted to a certain extent. For all the above process steps, it is within the scope of the skilled person to control the amount of liquid appropriately.

Additional Process Step (v)—Sulfiding

The tetrametallic bulk catalyst is generally used in its sulfided form. Catalyst sulfiding can be carried out in any way effective for making the catalyst in sulfide form, including conventional sulfiding methods. Sulfidation can be carried out by contacting the catalyst precursor, directly after its preparation or after any one of additional process steps (i)-(iv), with a sulfur-containing compound such as elemental sulfur, hydrogen sulfide, dimethyl disulfide, or organic or inorganic polysulfides. The sulfidation step can be carried out in the liquid and the gaseous phase.

The sulfidation can generally be carried out in-situ and/or ex-situ. Preferably, the sulfidation is carried out in-situ (i.e., the sulfidation is carried out in the hydroprocessing reactor subsequent to the bulk catalyst precursor composition being loaded into the hydroprocessing unit).

Use in Hydroprocessing

The bulk catalyst precursor of the present disclosure is particularly useful for hydroprocessing hydrocarbon feedstocks. Hydroprocessing includes processes such as hydrodesulfurization, hydrodenitrogenation, hydrodemetallation, hydrodearomatization, hydrogenation, hydrogenolysis, hydrotreating, hydroisomerizaiton, and hydrocracking.

A wide range of petroleum and chemical hydrocarbon feedstocks can be hydroprocessed in accordance with the present disclosure. Hydrocarbon feedstocks include those obtained or derived from crude petroleum oil, from tar sands, from coal liquefaction, from shale oil and from hydrocarbon synthesis, such as reduced crudes, hydrocrackates, raffinates, hydrotreated oils, atmospheric and vacuum gas oils, coker gas oils, atmospheric and vacuum residua, deasphalted oils, dewaxed oils, slack waxes, Fischer-Tropsch waxes, biorenewable feedstocks, and mixtures thereof. Suitable feedstocks range from relatively light distillate fractions up to heavy feedstocks, such as gas oils, lube oils and residua. Examples of light distillate feedstocks include naphtha (typical boiling range of from about 25° C. to about 210° C.), diesel (typical boiling range of from about 150° C. to about 400° C.), kerosene or jet fuel (typical boiling range of from about 150° C. to about 250° C.) and the like. Examples of heavy feedstocks include vacuum (or heavy) gas oils (typical boiling range of from about 315° C. to about 610° C.), raffinates, lube oils, cycle oils, waxy oils and the like. Preferred hydrocarbon feedstocks have a boiling range of from about 150° C. to about 650° C. (e.g., from about 150° C. to about 450° C.).

Hydroprocessing conditions can include a temperature of from 200° C. to 450° C., or from 315° C. to 425° C.; a pressure of from 250 to 5000 psig (1.7 to 34.6 MPa), or from 300 to 3000 psig (2.1 to 20.7 MPa); a liquid hourly space velocity (LHSV) of from 0.1 to 10 $h^{-1}$, or from 0.5 to 5 $h^{-1}$;

and a hydrogen gas rate of from 100 to 15,000 SCF/B (17.8 to 2672 m³/m³), or from 500 to 10,000 SCF/B (89 to 1781 m³/m³).

Hydroprocessing according to the present disclosure can be practiced in one or more reaction zones using any suitable reactor system such as one or more fixed-bed, moving-bed or fluidized bed reactors. A fixed bed reactor can include one or more vessels, single or multiple beds of catalyst in each vessel, and various combinations of hydroprocessing catalyst in one or more vessels.

EXAMPLES

The following illustrative examples are intended to be non-limiting.

Example 1 (Comparative)

Synthesis of Bulk Catalyst Precursor

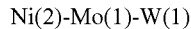

Ni(2)-Mo(1)-W(1)

Preparation of Solution A: 70.6 g of ammonium heptamolybdate and 102.0 g of ammonium metatungstate hydrate were added into 2000 g of deionized water in a 4 L flask. The pH was adjusted to 9.8 with ammonia water. The solution was then heated to 80° C.

Preparation of Solution B: In a separate 500 mL beaker, 232.6 g of nickel nitrate and 13.9 of maleic acid were dissolved into 100 g of deionized water.

Solution B was added into Solution A at a rate of 10 mL/min. The pH was monitored during addition. Green precipitates formed as soon as Solution B was added. The final pH was at 6.0-7.0 after addition. The slurry was aged at 80° C. for 4 hours.

The slurry was filtered, and the wet cake collected. The wet cake was washed with 300 g of deionized water to remove ammonium nitrate by-product. The wet cake was then dried in an oven at 130° C. to remove any moisture.

Example 2 (Comparative)

Synthesis of Bulk Catalyst Precursor

Ni—Mo—W—Co

Preparation of Solution A: 45.0 g of ammonium heptamolybdate and 58.0 g of ammonium metatungstate were added into 2500 g of deionized water in a 4 L flask. The pH was adjusted to 9.8 with ammonia water. The solution was then heated to 80° C.

Preparation of Solution B: In a separate 500 mL beaker, 140.0 g of nickel nitrate, 140.0 g of cobalt nitrate, and 16.0 g of maleic acid were dissolved into 125 g of deionized water.

Solution B was added into Solution A at a rate of 10 mL/min. The pH was monitored during addition. Green precipitates formed as soon as Solution B was added. The final pH was at 6.0-7.0 after addition. The slurry was aged at 80° C. for 4 hours.

The slurry was filtered, and the wet cake collected. The wet cake was washed with 300 g of deionized water to remove ammonium nitrate by-product. The wet cake was then dried in an oven at 130° C. to remove any moisture.

Example 3

Synthesis of Bulk Catalyst Precursor

Ni—Mo—W—Ti

With Ex-Situ Addition of Ti

Preparation of Solution A: 10.4 g of ammonium heptamolybdate and 44.8 g of ammonium metatungstate were added into 1000 g of deionized water in a 4 L flask. The pH was adjusted to 9.8 with ammonia water. The solution was then heated to 80° C.

Preparation of Solution B: In a separate 500 mL beaker, 128.5 g of nickel nitrate and 7.1 g of maleic acid were dissolved into 100 g of deionized water.

Solution B was added into Solution A at a rate of 10 mL/min. The pH was monitored during addition. Green precipitates formed as soon as Solution B was added. The final pH was at 6.0-7.0 after addition. The slurry was aged at 80° C. for 4 hours.

The slurry was filtered, and the wet cake collected. The wet cake was washed with 300 g of deionized water to remove ammonium nitrate by-product. The wet cake was transferred into a beaker and heated at 60° C. with stirring. Then, 100 g of hydrophilic fumed TiO₂ (AEROXIDE® TiO₂ P25, Evonik) was mixed into the wet cake until the mixture was homogeneous. The wet cake was dried at 130° C. to remove any moisture.

Example 4

Synthesis of Bulk Catalyst Precursor

Ni—Mo—W—Ti

With In-Situ Addition of Ti

Preparation of Solution A: 10.4 g of ammonium heptamolybdate 44.8 g of ammonium metatungstate were added into 1000 g of deionized water in a 4 L flask. The pH was adjusted to 9.8 with ammonia water. The solution was then heated to 80° C.

Preparation of Gel C: In a 500 mL beaker, 128.3 g of nickel nitrate was dissolved in 210 g of ethylene glycol. In a separate 1 L beaker, 116.1 g of titanium tetra-n-butoxide [Ti(OBu)₄] was mixed into 1200 g of ethylene glycol. The Ti(OBu)₄/ethylene glycol solution was added to the nickel nitrate/ethylene glycol solution at a rate of 5 mL/min. Gel C was aged at 80° C. for 2 hours.

Gel C was then added into Solution A at a rate of 10 mL/min. The pH was monitored during addition. Green precipitates formed upon addition of Gel C. The final pH was at 6.0-7.0 after addition. The slurry was aged at 80° C. for 4 hours.

The slurry was filtered, and the wet cake collected. The wet cake was washed with 300 g of deionized water to remove ammonium nitrate by-product and ethylene glycol. The wet cake was dried at 130° C. to remove any moisture.

Figure 3:
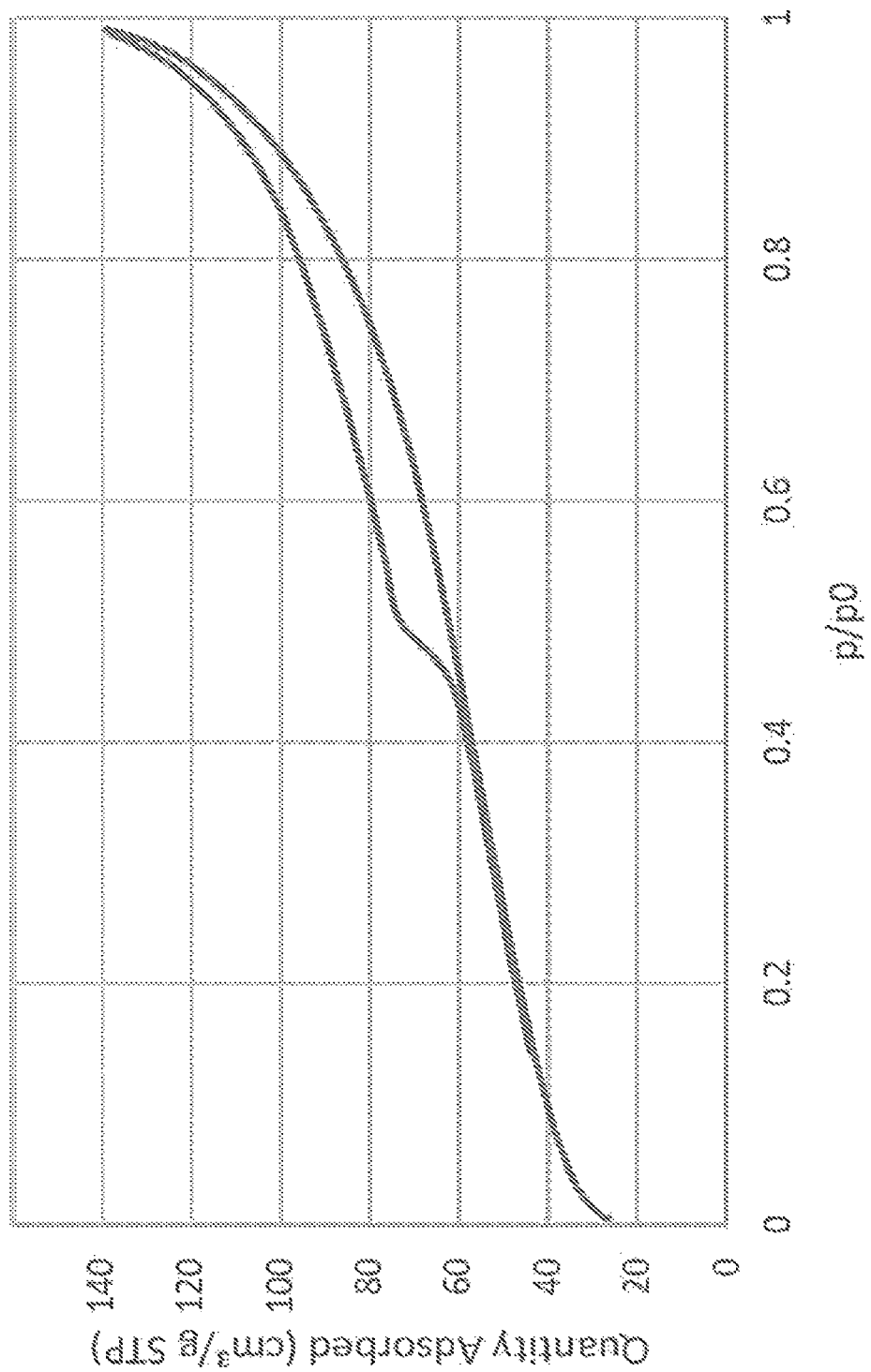
FIG. 3 shows an isotherm plot of $N_2$ physisorption conducted at 77 K on the Ni—Mo—W—Ti catalyst precursor of Example 4.

FIG. 3 shows the isotherm plot of N₂ physisorption conducted at 77 K on the catalyst precursor. FIG. 3 indicates that this material has type B slit-shaped porosity.

Figure 4:
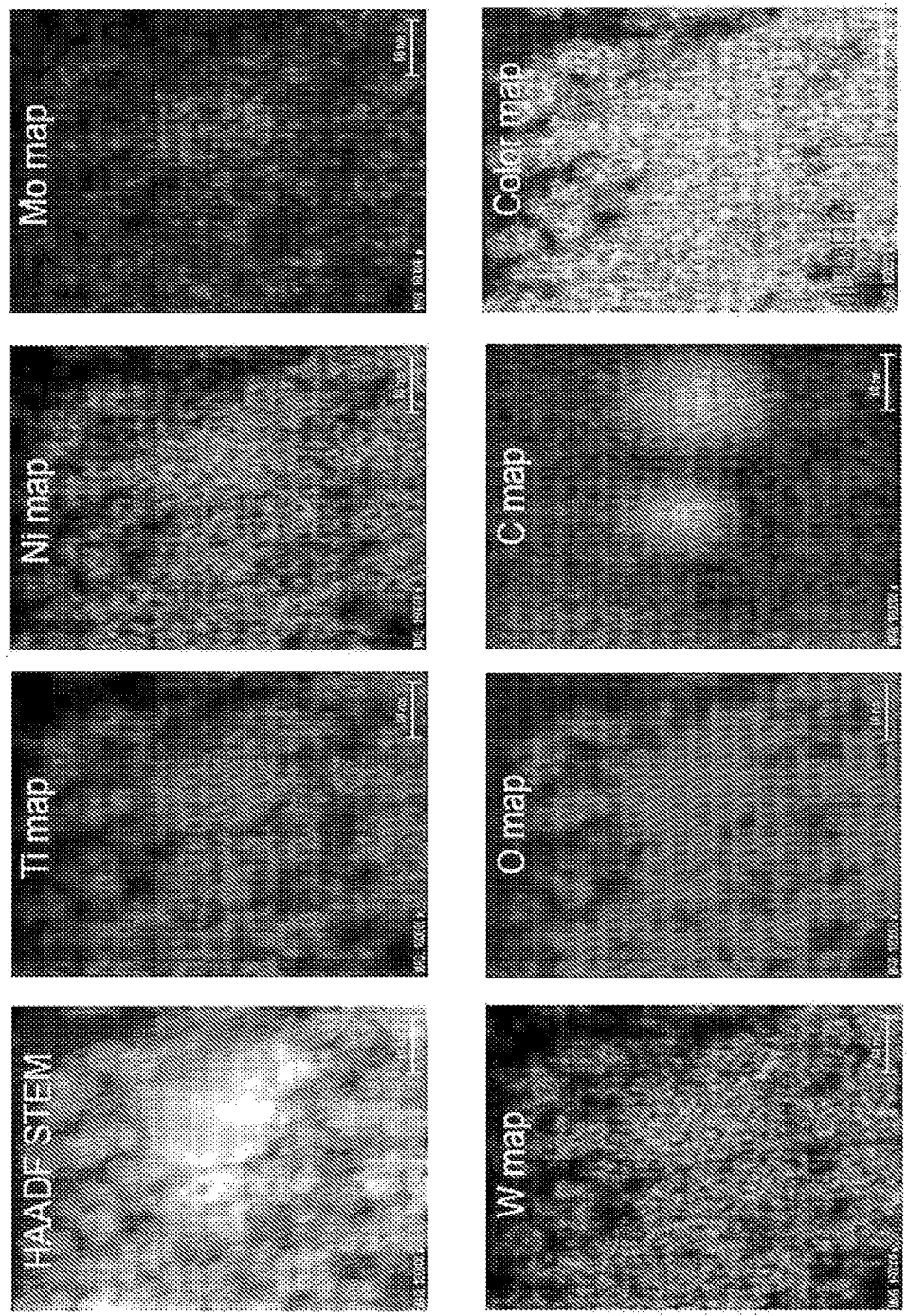
FIG. 4 displays High-Angle Annular Dark-Field Scanning Transmission Electron Microscopy (HAADF-STEM) images obtained for the Ni—Mo—W—Ti catalyst precursor of Example 4.

FIG. 4 displays HAADF-STEM images obtained for the catalyst precursor. FIG. 4 indicates that all four metal oxides are homogeneously distributed. No islands of $TiO_2$ are observed.

Example 5

Synthesis of Bulk Catalyst Precursor

Ni—Mo—W—Ti

With In-Situ Addition of Ti

Example 4 was repeated except that 766.1 g of titanium tetra-n-butoxide was used.

Figure 5:
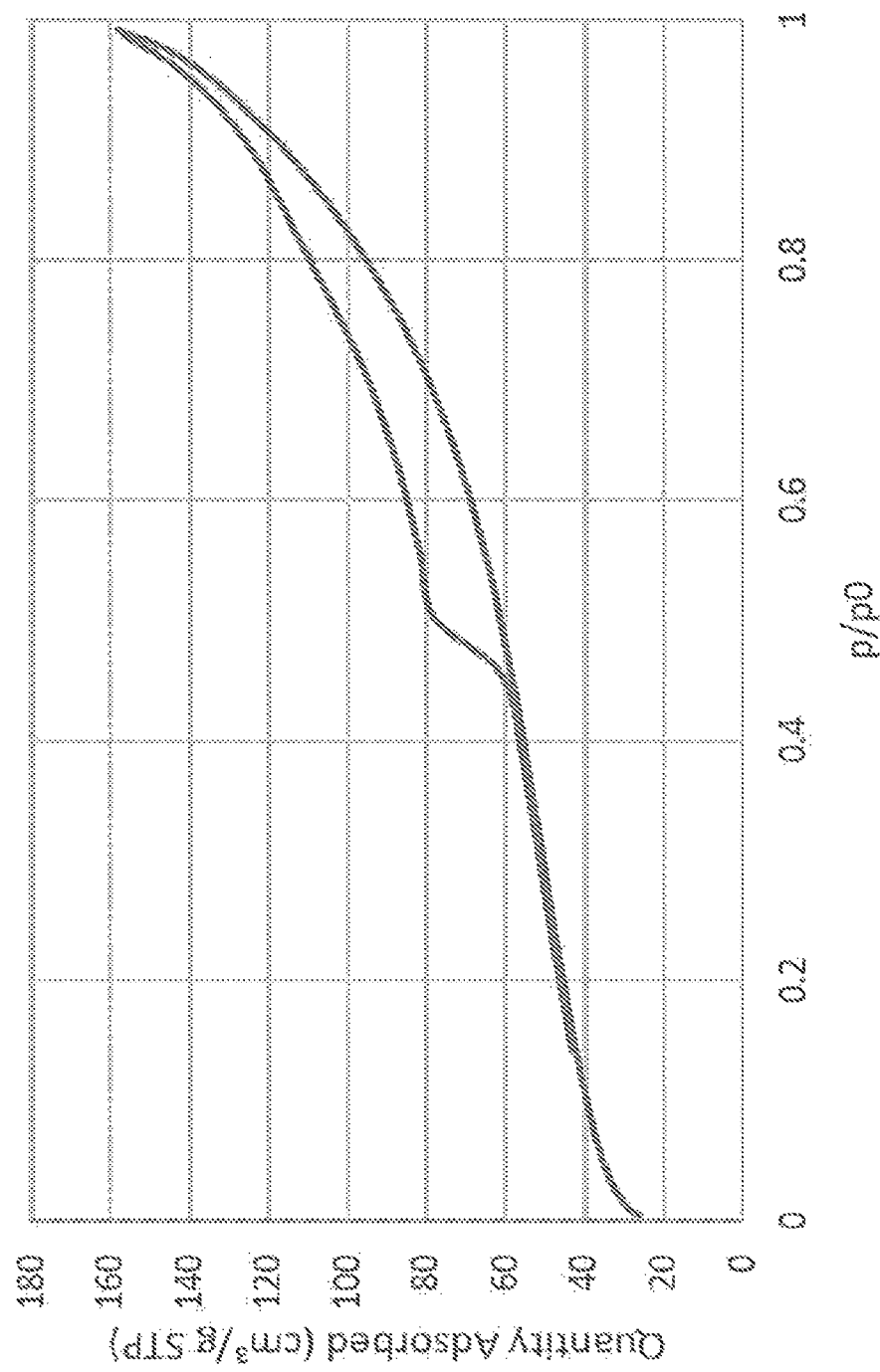
FIG. 5 shows an isotherm plot of $N_2$ physisorption conducted at 77 K on the Ni—Mo—W—Ti catalyst precursor of Example 5.

FIG. 5 shows the isotherm plot of $N_2$ physisorption conducted at 77 K on the catalyst precursor. FIG. 5 indicates that this material has a type B slit-shaped porosity.

Example 6

Production of Extrudates

Prior to catalytic evaluation, catalyst precursors were shaped into extrudates. Dried catalyst precursor was ground to a fine powder (<100 mesh) and mixed with a proper amount of a binder and water to make an extrudable mixture, followed by extrusion on a Carver press.

Example 7

Bulk Catalyst Precursor Characterization

The particle density (D), BET surface area (SA) and pore volume (PV) were measured for the bulk catalyst precursors of Examples 1-5. The results are shown in Table 1 below. Table 1 shows addition of $TiO_2$ can improve pore volume and decrease particle density.

TABLE 1

| Precursor | Composition | D [g/cm³] | $N_2$ BET SA [m²/g] | $N_2$ PV [cm³/g] |
|---|---|---|---|---|
| Example 1 | Ni—Mo—W | 2.45 | 124 | 0.09 |
| Example 2 | Ni—Mo—W—Co | 2.47 | 136 | 0.09 |
| Example 3 | Ni—Mo—W—Ti | 1.94 | 118 | 0.11 |
| Example 4 | Ni—Mo—W—Ti | 1.67 | 164 | 0.20 |
| Example 5 | Ni—Mo—W—Ti | 2.14 | 159 | 0.23 |

Example 8

Catalyst Evaluation—Hydrogenolysis of Tetralin

Catalyst precursor extrudates from Examples 1 and 3-4 were tested for tetralin hydrogenolysis activity in a fixed bed reactor. All catalyst precursors were pre-sulfided using tetralin spiked with 300 wppm of sulfur in the form of dimethyl disulfide. The catalyst precursors were sulfided using the spiked tetralin feed at 450° F. and 800 psig $H_2$ pressure for 24 hours and then ramped to 650° F. at 25° F./hour and held at 650° F./800 psig for 10 hours.

The catalyst was evaluated at a reactor total pressure of 2300 psig, a hydrogen feed rate of 8000 SCF/B, and a LHSV of 1 $h^{-1}$. The tetralin feed contained 300 wppm sulfur.

Table 2 shows the hydrogenolysis performance of each catalyst.

TABLE 2

| | Yield of Ring-Opening Products (%) | | | |
|---|---|---|---|---|
| Temp. [° F.] | Example 1 [Ni—Mo—W] | Example 3 [Ni—Mo—W—Ti] | Example 4 [Ni—Mo—W—Ti] | $TiO_2^{(a)}$ |
| 620 | 0.4 | 0.4 | 0.3 | 0.1 |
| 640 | 1.2 | 1.3 | 1.5 | 0.4 |
| 660 | 3.6 | 3.9 | 3.7 | 0.2 |
| 680 | 8.8 | 8.0 | 9.3 | 0.2 |
| 700 | 16.0 | 17.2 | 18.5 | 0.2 |
| 720 | 26.0 | 27.6 | 34.9 | 0.4 |
| 740 | 37.6 | 40.0 | 50.2 | 0.7 |

$^{(a)}$Hydrophilic fumed $TiO_2$ (AREOXIDE ® $TiO_2$ P 25, Evonik).

The results show that the activity of the bulk catalyst of Example 3 is comparable to the conventional bulk catalyst of Example 1, although the bulk catalyst has a lesser amount of active metals (i.e., Ni, Mo and W). The activity of the bulk catalyst of Example 4 is significantly higher than the bulk catalysts of Examples 1 and 3, at higher temperatures. Without being bound by any theory, it is believed that the in-situ route to introduce $TiO_2$ leads to higher dispersion of metals and increases acidity of the catalyst considerably. The $TiO_2$ control catalyst itself does not have sufficient activity to open rings in any substantial amount.

Example 9 (Comparative)

Synthesis of Bulk Catalyst Precursor

Ni(2.5)-Mo(1)-W(1.1)

Preparation of Solution A: 45 g of ammonium heptamolybdate and 72 g of ammonium metatungstate were added into 2000 g of deionized water in a 4 L flask. The pH was adjusted to 9.8 with ammonia water and the solution heated up to 80° C.

Preparation of Solution B: 184.5 g of nickel nitrate and 10.1 g of maleic acid were dissolved into 100 g of deionized water.

Solution B was added into Solution A within 15 minutes. Green precipitates were formed during the addition of Solution B. The final pH was at 6.0-7.0. The slurry was aged with stirring at 80° C. for 4 hours. After ageing, the product was recovered by filtration, washed with deionized water and dried at 130° C.

Example 10 (Comparative)

Synthesis of Bulk Catalyst Precursor

Ni(7.5)-Mo(1)-W(3)

Example 9 was repeated, except that the following reagents were used in the amounts indicated in parentheses: ammonium heptamolybdate (10.4 g), ammonium metatungstate (44.8 g), maleic acid (5.8 g) and nickel nitrate (128.3 g).

Example 11 (Comparative)

Synthesis of Bulk Catalyst Precursor

Ni(3.8)-Mo(1)-W(1.1)

Example 9 was repeated, except that the following reagents were used in the amounts indicated in parentheses: ammonium molybdate (17.6 g), ammonium heptamolybdate (27.8 g), maleic acid (5.8 g) and nickel nitrate (110.3 g).

Example 12

Synthesis of Bulk Catalyst Precursor

Ni(2.5)-Mo(1)-W(1.1)-Ti(2.7)

With In-Situ Addition of Ti

Preparation of Slurry A: 45 g of ammonium heptamolybdate, 72 g of ammonium metatungstate and 56 g of $TiO_2$ (Venator Hombikat 8602) were added into 2000 g of deionized water in a 4 L flask. The pH was adjusted to 9.8 with ammonia water and the solution heated up to 80° C.

Preparation of Solution B: 184.5 g of nickel nitrate and 10.1 g of maleic acid were dissolved into 100 g of deionized water.

Solution B was added into Slurry A within 15 minutes. Green precipitates were formed during the addition of Solution B. The final pH was at 6.0-7.0. The slurry was aged with stirring at 80° C. for 4 hours. After ageing, the product was recovered by filtration, washed with deionized water and dried at 130° C.

Example 13

Synthesis of Bulk Catalyst Precursor

Ni(2.5)-Mo(1)-W(1.1)-Ti(2.7)

With Ex-Situ Addition of Ti

Preparation of Solution A: 45 g of ammonium heptamolybdate and 72 g of ammonium metatungstate were added into 2000 g of deionized water in a 4 L flask. The pH was adjusted to 9.8 with ammonia water and the solution heated up to 80° C.

Preparation of Solution B: 184.5 g of nickel nitrate and 10.1 g of maleic acid were dissolved into 100 g of deionized water.

Solution B was added into Solution A within 15 minutes. Green precipitates were formed during the addition of Solution B. The final pH was at 6.0-7.0. The slurry was aged with stirring at 80° C. for 4 hours. After ageing, the product was recovered by filtration. The filter cake and 56 g of $TiO_2$ (Venator Hombikat 8602) were mixed to homogeneity and stirred at 80° C. for 2 hours. The mixture was recovered by filtration, washed with deionized water and dried at 130° C.

Example 14

Synthesis of Bulk Catalyst Precursor

Ni(2.5)-Mo(1)-W(1.1)-Ti(2.7)

Example 12 was repeated except that Venator Hombikat ADW-1 $TiO_2$ was used as the source of $TiO_2$.

Example 15

Synthesis of Bulk Catalyst Precursor

Ni(6.6)-Mo(1)-W(3)-Ti(9.8)

With Ex-Situ Addition of Ti

Preparation of Solution A: 32 g of ammonium heptamolybdate and 139.4 g of ammonium metatungstate were added into 2000 g of deionized water in a 4 L flask. The pH was adjusted to 9.8 with ammonia water and the solution heated up to 80° C.

Preparation of Solution B: 354.7 g of nickel nitrate and 10.1 g of maleic acid were dissolved into 100 g of deionized water.

Solution B was added into Solution A within 15 minutes. Green precipitates were formed during the addition of Solution B. The final pH was at 6.0-7.0. The slurry was aged with stirring at 80° C. for 4 hours. After ageing, the product was recovered by filtration. The filter cake and 56 g of $TiO_2$ (Evonik AEROXIDE® E0167) were mixed to homogeneity and stirred at 80° C. for 2 hours. The mixture was recovered by filtration, washed with deionized water and dried at 130° C.

Example 16

Synthesis of Bulk Catalyst Precursor

Ni(6.6)-Mo(1)-W(3)-Ti(5)

Example 14 was repeated except that 93.1 of $TiO_2$ (Evonik AEROXIDE® E0167) was used.

Example 17

Synthesis of Bulk Catalyst Precursor

Ni(6.6)-Mo(1)-W(3)-Ti(2.5)

Example 14 was repeated except that 46.6 of $TiO_2$ (Evonik AEROXIDE® E0167) was used.

Example 18

Synthesis of Bulk Catalyst Precursor

Ni(2.5)-Mo(1)-W(1.1)-Ti(3)

With In-Situ Addition of Ti Compound

Preparation of Solution A: 45 g of ammonium heptamolybdate and 72 g of ammonium metatungstate were added into 2000 g of deionized water in a 4 L flask. The pH was adjusted to 9.8 with ammonia water and the solution heated up to 80° C.

Preparation of Gel C: 184.3 g of nickel nitrate was dissolved in 210 g of ethylene glycol. In a separate 1 L beaker, 321.6 g of Ti(OBu)$_4$ was mixed into 1200 g of ethylene glycol. The Ti(OBu)$_4$ mixture was then added to the Nickel nitrate mixture at a rate of 5 mL/min with vigorous mixing. The resulting gel was aged at 80° C. for 2 hours.

Gel C was added into solution A within 15 minutes. Green precipitates were formed during the addition of gel C. The final pH was at 6.0-7.0. The slurry was aged with stirring at 80° C. for 4 hours. After ageing, the product was recovered by filtration, washed with deionized water and dried at 130° C.

Example 19

Synthesis of Bulk Catalyst Precursor

Ni(7.5)-Mo(1)-W(3)-Ti(3.8)

Example 16 was repeated except that 128.3 g of nickel nitrate was dissolved in 210 g of ethylene glycol and that 76.1 g of Ti(OBu)$_4$ was mixed into 230 g of ethylene glycol.

Example 20

Synthesis of Bulk Catalyst Precursor

Ni(2.5)-Mo(1)-W(1.1)-Ti(2.7)

Example 12 was repeated except that anatase nanopowder (99.5% 5 nm) from U.S. Research Nanomaterials, Inc. was used as the source of TiO$_2$.

Example 21

Synthesis of Bulk Catalyst Precursor

Ni(7.5)-Mo(1)-W(3)-Ti(21.2)

With Ex-Situ Addition of Ti

Preparation of Solution A: 10.4 g of ammonium heptamolybdate and 44.8 g of ammonium metatungstate were added into 1000 g of deionized water in a 4 L flask. The pH was adjusted to 9.8 with ammonia water and the solution heated up to 80° C.

Preparation of Solution B: 128.5 g of nickel nitrate and 7.1 g of maleic acid were dissolved into 100 g of deionized water.

Solution B was added into Solution A within 15 minutes. Green precipitates were formed during the addition of Solution B. The final pH was at 6.0-7.0. The slurry was aged with stirring at 80° C. for 4 hours. After ageing, the product was recovered by filtration. The filter cake and 100 g of hydrophilic fumed TiO$_2$ (Evonik AEROXIDE® P 25) were mixed to homogeneity and stirred at 80° C. for 2 hours. The mixture was recovered by filtration, washed with deionized water and dried at 130° C.

Example 22

Synthesis of Bulk Catalyst Precursor

Ni(2.5)-Mo(1)-W(1.1)-Ti(2.7)

Example 12 was repeated except that Venator Hombikat S141 was used as the source of TiO$_2$.

Example 23

Synthesis of Bulk Catalyst Precursor

Ni(2.5)-Mo(1)-W(1.1)-Ti(6.2)

Example 12 was repeated except that Venator S141 was used as the source of TiO$_2$ and in an amount of 128 g.

Example 24

Synthesis of Bulk Catalyst Precursor

Ni(2.5)-Mo(1)-W(1.1)-Ti(2.7)

With In-Situ Addition of Ti

Preparation of Slurry A: 56 g of ammonium heptamolybdate, 90 g of ammonium metatungstate and 467 g of colloidal TiO$_2$ (15 wt. % TiO$_2$ solids, Cerion Nanomaterials) were added into 2000 g of deionized water in a 4 L flask. The pH was adjusted to 9.8 with ammonia water and the solution heated up to 80° C.

Preparation of Solution B: 230 g of nickel nitrate and 10.1 g of maleic acid were dissolved into 100 g of deionized water.

Solution B was added into Slurry A within 15 minutes. Green precipitates were formed during the addition of Solution B. The final pH was at 6.0-7.0. The slurry was aged with stirring at 80° C. for 4 hours. After ageing, the product was recovered by filtration, washed with deionized water and dried at 130° C.

Example 25 (Comparative)

Synthesis of Bulk Catalyst Precursor

Ni(7.5)-Mo(1)-W(3)-Si(2)

With Ex-Situ Addition of Silicon

Preparation of Solution A: 10.4 g of ammonium heptamolybdate and 44.8 g of ammonium tungstate were added into 1000 g of deionized water in a 4 L flask. The pH was adjusted to 9.8 with ammonia water and the solution heated up to 80° C.

Preparation of Solution B: 128.5 g of nickel nitrate and 7.1 g of maleic acid were dissolved into 100 g of deionized water.

Solution B was added into Solution A within 15 minutes. Green precipitates were formed during the addition of Solution B. The final pH was at 6.0-7.0. The slurry was aged with stirring at 80° C. for 4 hours. After ageing, the product was recovered by filtration. The filter cake and 8.9 g of tetraethyl orthosilicate (TEOS) were mixed to homogeneity and stirred at 80° C. for 2 hours. The mixture was recovered by filtration, washed with deionized water and dried at 130° C.

Example 26 (Comparative)

Bulk Catalyst Precursor

Ni(6.6)-Mo(1)-W(3)-Si(6.6)

With Ex-Situ Addition of Silicon

Preparation of Solution A: 32.4 g of ammonium heptamolybdate and 139.4 g of ammonium tungstate were added into 2000 g of deionized water in a 4 L flask. The pH was adjusted to 9.8 with ammonia water and the solution heated up to 80° C.

Preparation of Solution B: 354.7 g of nickel nitrate and 10.1 g of maleic acid were dissolved into 100 g of deionized water.

Solution B was added into Solution A within 15 minutes. Green precipitates were formed during the addition of Solution B. The final pH was at 6.0-7.0. The slurry was aged with stirring at 80° C. for 4 hours. After ageing, the product was recovered by filtration. The filter cake and 91 g of silica gel (Davisil Grade 636) were mixed to homogeneity and stirred at 80° C. for 2 hours. The mixture was recovered by filtration, washed with deionized water and dried at 130° C.

Example 27 (Comparative)

Synthesis of Bulk Catalyst Precursor

Ni(6.6)-Mo(1)-W(3)-Si(2.9)

Example 27 was repeated except that 39 g of the silica gel was used.

Example 28 (Comparative)

Synthesis Bulk Catalyst Precursor

Ni(2.5)-Mo(1)-W(1.1)-Zr(1.8)

With Ex-Situ Addition of Zirconium

Preparation of Solution A: 45 g of ammonium heptamolybdate and 72 g of ammonium tungstate were added into 2000 g of deionized water in a 4 L flask. The pH was adjusted to 9.8 with ammonia water and the solution heated up to 80° C.

Preparation of Solution B: 184.5 g of nickel nitrate and 10.1 g of maleic acid were dissolved into 100 g of deionized water.

Solution B was added into Solution A within 15 minutes. Green precipitates were formed during the addition of Solution B. The final pH was at 6.0-7.0. The slurry was aged with stirring at 80° C. for 4 hours. After ageing, the product was recovered by filtration. The filter cake and 56 g of calcined $ZrO_2$ (Aldrich) were mixed to homogeneity and stirred at 80° C. for 2 hours. The mixture was recovered by filtration, washed with deionized water and dried at 130° C.

Example 29 (Comparative)

Bulk Catalyst Precursor

Ni(6.6)-Mo(1)-W(3)-C(14.5)

With Ex-Situ Addition of Carbon

Example 27 was repeated except that 39 g of the activated carbon (DARCO® G-60) was used instead of silica gel.

Example 30

Catalyst Evaluation—Vacuum Gas Oil Hydroconversion

Bulk catalyst precursor extrudates from Examples 9-11, 15-17 and 25-29 were sulfided and evaluated for catalytic activity with a VGO feed in a tri-phase fixed bed reactor.

Catalyst precursors were sulfided at 482° F./800 psig (250° C./5.5 MPa) for 5 hours and then ramped to 572° F. (300° C.) at 30° F./hour and soaked for 5 hours, and then ramped to 650° F./800 psig (343° C./5.5 MPa) at 30° F./hour and soaked for 6 hours.

Hydroprocessing conditions included a pressure of 2300 psig, a LHSV of 2 $h^{-1}$, and a $H_2$ treat gas rate of 4880 SCF/B.

Catalytic activity was compared based on the temperature for 10 ppm N with the particle density normalized to 2.5 $g/cm^3$. The results are summarized in Table 3.

TABLE 3

| Catalyst | Additive Added into Ni—Mo—W | Particle Density [$g/cm^3$] | Temperature [° F.] |
|---|---|---|---|
| Example 9 | — | 2.66 | 702 |
| Example 10 | — | 2.38 | 698 |
| Example 11 | — | 2.19 | 704 |
| Example 15 | $TiO_2$ | 2.09 | 703 |
| Example 16 | $TiO_2$ | 2.16 | 701 |
| Example 17 | $TiO_2$ | 2.06 | 698 |
| Example 25 | $SiO_2$ | 2.05 | 708 |
| Example 26 | $SiO_2$ | 1.26 | 712 |
| Example 27 | $SiO_2$ | 2.21 | 710 |
| Example 28 | $ZrO_2$ | 1.97 | 717 |
| Example 29 | C | 1.60 | 705 |

The results in Table 3 show that addition of $TiO_2$ in various amounts decreases particle density without sacrificing activity as the temperature needed to reach HDN target stays the same as Ni—Mo—W catalyst. In comparison, addition of $SiO_2$, $ZrO_2$ and C decreases the activity although it also decreases particle density.

Example 31

Catalyst Evaluation—Tetralin Hydrogenolysis

Ni—Mo—W bulk catalyst precursors of Examples 10-11 and Ni—Mo—W—Ti bulk catalyst precursors of Examples 14, 18 and 20-24 were tested for tetralin hydrogenolysis activity in a tri-phase fixed bed reactor as described in Example 9.

The catalyst evaluation conditions included a reactor pressure of 2300 psig, a hydrogen feed rate of 3500 SCF/B, and a LHSV of 1 $h^{-1}$. The tetralin feed contained 300 wppm sulfur.

Table 4 summarizes the ring opening activity of the catalysts.

TABLE 4

| Temp. | Yield of Ring Opening Products [%] | | | | | | | | |
|---|---|---|---|---|---|---|---|---|---|
| [° F.] | TiO$_2$[a] | Ex. 10 | Ex. 11 | Ex. 14 | Ex. 18 | Ex. 20 | Ex. 21 | Ex. 22 | Ex. 23 | Ex. 24 |
| 640 | 0.4 | 1.2 | 1.2 | 0.4 | 1.5 | 0.8 | 0.9 | 1.0 | 1.0 | 1.2 |
| 660 | 0.2 | 3.6 | 2.1 | 2.0 | 3.7 | 2.5 | 1.8 | 2.9 | 1.9 | 2.9 |
| 680 | 0.2 | 8.8 | 4.6 | 3.4 | 9.3 | 6.9 | 3.9 | 6.0 | 3.5 | 5.8 |
| 700 | 0.2 | 16.0 | 8.4 | 7.2 | 18.5 | 14.2 | 12.6 | 13.4 | 7.4 | 14.0 |
| 720 | 0.4 | 26.0 | 14.1 | 21.1 | 34.9 | 28.8 | 20.1 | 24.6 | 14.5 | 23.6 |
| 740 | 0.7 | 37.6 | 22.6 | 37.2 | 50.2 | 45.7 | 29.8 | 37.7 | 24.1 | 32.6 |

[a]Hydrophilic fumed TiO$_2$ (AEROXIDE ® P 25, Evonik)

The results in Table 4 indicate that for the ring opening of tetralin, TiO$_2$ by itself without Ni—Mo—W does not have any activity. The Ni—Mo—W—Ti systems have various levels of activity which depends on the type of TiO$_2$ and methods of preparation. Selection of TiO$_2$ type and preparation can potentially provide benefits in both low particle density and enhanced ring opening activity.

Example 32

Catalytic Testing—Hydroconversion of a Straight-Run Diesel/Tetralin Feed

Ni—Mo—W bulk catalyst precursors of Examples 9-11 and Ni—Mo—W—Ti bulk catalyst precursors of Examples 14, 18 and 22-23 were tested for catalytic activity in a fixed bed reactor with a 30 vol. % straight-run diesel/70 vol. % tetralin blend feed. Catalytic activity was compared based on conversion of polynuclear aromatic compounds (PNAs).

Catalyst precursors were sulfided as described in Example 8.

Hydroprocessing conditions included a pressure of 1200 psig, a LHSV of 1 h$^{-1}$, and a H$_2$ gas rate of 3500 SCF/B.

Table 5 summarizes the ring opening activity of the catalysts.

TABLE 5

| Temp. | Conversion of PNAs [%] | | | | | | |
|---|---|---|---|---|---|---|---|
| [° F.] | Ex. 9 | Ex. 10 | Ex. 11 | Ex. 14 | Ex. 18 | Ex. 22 | Ex. 23 |
| 640 | 21.4 | 20.8 | 21.2 | 19.9 | 16.9 | 20.4 | 18.7 |
| 680 | 28.4 | 27.4 | 29.1 | 26.1 | 24.5 | 27.9 | 25.4 |
| 700 | 30.7 | 29.9 | 30.2 | 30.0 | 26.8 | 29.4 | 28.2 |
| 720 | 28.3 | 29.8 | 28.7 | 28.3 | 26.2 | 28.9 | 27.9 |
| 740 | 24.6 | 24.7 | 23.9 | 23.8 | 24.5 | 24.4 | 23.8 |
| 760 | 19.1 | 19.1 | 18.1 | 18.6 | 18.2 | 19.6 | 18.7 |

The results in Table 5 show that Ni—Mo—W—Ti systems have comparable activity with Ni—Mo—W systems for hydroconversion of the straight-run diesel/tetralin feed.

Example 33 (Comparative)

Synthesis of Trimetallic Bulk Catalyst Precursor

Ni(1.25)-Mo(1)-Ti(1.12)

Preparation of Slurry A: 112 g of ammonium heptamolybdate and 57 g of TiO$_2$ (Venator S141) were added into 3200 g of deionized water in a 4 L flask. The pH was adjusted to 9.8 with ammonia water and the solution heated up to 80° C.

Preparation of Solution B: 230 g of nickel nitrate and 12.6 g of maleic acid were dissolved into 100 g of deionized water.

Solution B was added into Slurry A within 15 minutes. Green precipitates were formed during the addition of Solution B. The final pH was at 6.0-7.0. The slurry was aged with stirring at 80° C. for 4 hours. After ageing, the product was recovered by filtration, washed with deionized water and dried at 130° C.

Example 34 (Comparative)

Synthesis of Trimetallic Bulk Catalyst Precursor

Ni(1.1)-W(1)-Ti(1.37)

Preparation of Slurry A: 182.7 g of ammonium metatungstate and 79 g of TiO$_2$ (Venator S141) were added into 3200 g of deionized water in a 4 L flask. The pH was adjusted to 9.8 with ammonia water and the solution heated up to 80° C.

Preparation of Solution B: 230 g of nickel nitrate and 12.6 g of maleic acid were dissolved into 100 g of deionized water.

Solution B was added into Slurry A within 15 minutes. Green precipitates were formed during the addition of Solution B. The final pH was at 6.0-7.0. The slurry was aged with stirring at 80° C. for 4 hours. After ageing, the product was recovered by filtration, washed with deionized water and dried at 130° C.

The invention claimed is:

1. A method for preparing a bulk catalyst from a bulk catalyst precursor having a formula of

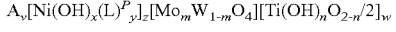

wherein:
(i) A is an alkali metal cation, a rare earth metal cation, an ammonium cation, an organic ammonium cation, phosphonium cation, or a combination thereof;
(ii) L is an organic compound-based component; and
(iii) 0≤y≤-2/p, 0≤x<2; 0≤v<2; 0<z; 0<m<1; 0<n<4; 0.1<w/(z+1)<10;

the method comprising:
(a) combining in a reaction mixture:
   (i) a Ni-containing precursor;
   (ii) a Mo-containing precursor;
   (iii) a W-containing precursor;
   (iv) a Ti-containing precursor;
   (v) an organic compound-based component; and
   (vi) a protic liquid; and
(b) reacting the mixture under conditions sufficient to cause precipitation of the bulk catalyst precursor, wherein the steps (a) and (b) are carried out at a temperature of no more than 200° C.;

(c) recovering a bulk catalyst precursor defined by a region of a quaternary phase diagram wherein the region is defined by ten points ABCDEFGHIJ and wherein the ten points, on a metal oxide basis (wt. %), are: A (Ni=39, Mo=1, W=41, Ti=20), B (Ni=39, Mo=1, W=72, Ti=20), C (Ni=9, Mo=17, W=54, Ti=20), D (Ni=31, Mo=25, W=24, Ti=20), E(Ni=40, Mo=14, W=f26, Ti=20), F(Ni=34, Mo=1, W=36, Ti=30), G (Ni=7, Mo=1, W=63, Ti=30), H(Ni=8, Mo=15, W=48, Ti=30), I(Ni=27, Mo=22, W=21, Ti=30), and J(Ni=35, Mo=12, W=23, Ti=30); and (d) sulfiding the bulk catalyst precursor to form a bulk catalyst.

2. The method of claim 1, wherein the reaction mixture is prepared by:
preparing a first mixture comprising a Ni-containing precursor, a protic liquid, and an organic compound-based component;
preparing a second mixture comprising a Mo-containing precursor, a W-containing precursor, and a protic liquid;
adding a Ti-containing precursor to the first mixture, the second mixture, or a combination thereof;
heating both the first and second mixtures to a temperature of from 60° C. to 150° C.; and
combining the first and second mixtures together.

3. The method of claim 2, wherein the Ti-containing precursor is selected from $TiO_2$ nanoparticles, colloidal $TiO_2$, fumed $TiO_2$, titanium hydroxide, organotitanium compounds, titanium halides, organotitanium halides, water-soluble titanium salts, or a combination thereof.

4. The method of claim 1, wherein the reacting is carried out at one or more temperatures either (a) in a range of 60° C. to 100° C. under atmospheric pressure or (b) above 100° C. under autogenous pressure.

5. The method of claim 1, wherein the organic compound-based component is selected from an organic acid or salt thereof, a sugar, a sugar alcohol, or a combination thereof.

6. The method of claim 5, wherein the organic compound-based component is selected from glyoxylic acid, pyruvic acid, lactic acid, malonic acid, oxaloacetic acid, malic acid, fumaric acid, maleic acid, tartaric acid, gluconic acid, citric acid, oxamic acid, serine, aspartic acid, glutamic acid, iminodiacetic acid, ethylenediaminetetraacetic acid, fructose, glucose, galactose, mannose, sucrose, lactose, maltose, erythritol, xylitol, mannitol, sorbitol, or a combination thereof.

7. The method of claim 1, further comprising one or more of the following steps:
compositing the bulk catalyst precursor with 0 to 40 wt. % with a material selected from the group consisting of binder materials, conventional hydroprocessing catalysts, cracking compounds, or mixtures thereof;
spray-drying, (flash) drying, milling, kneading, slurry-mixing, dry or wet mixing, or combinations thereof;
shaping, or
drying and/or thermally treating at a temperature of no more than 200° C.

8. The method of claim 1, wherein the Ti-containing precursor is an organotitanium precursor.

9. The method of claim 8, wherein the organotitanium precursor comprises a titanium alkoxide.

10. A method for preparing a bulk catalyst from a bulk catalyst precursor having a formula of

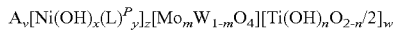

$A_v[Ni(OH)_x(L)^P_y]_z[Mo_mW_{1-m}O_4][Ti(OH)_nO_{2-n}/2]_w$ wherein:
(i) A is an alkali metal cation, a rare earth metal cation, an ammonium cation, an organic ammonium cation, phosphonium cation, or a combination thereof;
(ii) L is an organic compound-based component; and
(iii) $0 \leq y \leq -2/p$; $0 \leq x < 2$; $0 \leq v < 2$; $0 < z$; $0 < m < 1$; $0 < n < 4$; $0.1 < w/(z+1) < 10$;

the method comprising:
(a) combining in a reaction mixture:
(i) a Ni-containing precursor;
(ii) a Mo-containing precursor;
(iii) a W-containing precursor;
(iv) an organic compound-based component; and
(v) a protic liquid; and
(b) reacting the mixture under conditions sufficient to cause precipitation of an intermediate bulk catalyst precursor; and
(c) compositing the intermediate bulk catalyst precursor with a Ti-containing precursor to form the bulk catalyst precursor;
wherein the steps (a)-(c) are carried out at a temperature of no more than 200° C.; and
(d) recovering a bulk catalyst precursor defined by a region of a quaternary phase diagram wherein the region is defined by ten points ABCDEFGHIJ and wherein the ten points, on a metal oxide basis (wt. %), are: A (Ni=39, Mo=1, W=41, Ti=20), B(Ni=39, Mo=1, W=72, Ti=20), C (Ni=9, Mo=17, W=54, Ti=20), D (Ni=31, Mo=25, W=24, Ti=20), E(Ni=40, Mo=14, W=26, Ti=20), F(Ni=34, Mo=1, W=36, Ti=30), G (Ni=7, Mo=1, W=63, Ti=30), H(Ni=8, Mo=15, W=48, Ti=30), I (Ni=27, Mo=22, W=21, Ti=30), and J(Ni=35, Mo=12, W=23, Ti=30); and
(e) sulfiding the bulk catalyst precursor to form a bulk catalyst.

11. The method of claim 10, wherein the reaction mixture is prepared by:
preparing a first mixture comprising a Ni-containing precursor, a protic liquid, and, optionally, an organic compound-based component;
preparing a second mixture comprising a Mo-containing precursor, a W-containing precursor, and a protic liquid;
heating both the first and second mixtures to a temperature of from 60° C. to 150° C.; and
combining the first and second mixtures together.

12. The method of claim 10, wherein the Ti-containing precursor is selected from $TiO_2$ nanoparticles, fumed $TiO_2$, or a combination thereof.

13. The method of claim 10, wherein the intermediate bulk catalyst precursor is a Ni—Mo—W bulk catalyst precursor.

14. The method of claim 10, wherein the reacting is carried out at one or more temperatures either (a) in a range of 60° C. to 100° C. under atmospheric pressure or (b) above 100° C. under autogenous pressure.

15. The method of claim 10, wherein the organic compound-based component is selected from an organic acid or salt thereof, a sugar, a sugar alcohol, or a combination thereof.

16. The method of claim 15, wherein the organic compound-based component is selected from glyoxylic acid, pyruvic acid, lactic acid, malonic acid, oxaloacetic acid, malic acid, fumaric acid, maleic acid, tartaric acid, gluconic acid, citric acid, oxamic acid, serine, aspartic acid, glutamic acid, iminodiacetic acid, ethylenediaminetetraacetic acid, fructose, glucose, galactose, mannose, sucrose, lactose, maltose, erythritol, xylitol, mannitol, sorbitol, or a combination thereof.

17. The method of claim 10, further comprising one or more of the following steps:
    compositing the bulk catalyst precursor with 0 to 40 wt. % with a material selected from the group consisting of binder materials, conventional hydroprocessing catalysts, cracking compounds, or mixtures thereof;
    spray-drying, (flash) drying, milling, kneading, slurry-mixing, dry or wet mixing, or combinations thereof;
    shaping, or
    drying and/or thermally treating at a temperature of no more than 200° C.

18. The method of claim 10, wherein the Ti-containing precursor is an organotitanium precursor.

19. The method of claim 18, wherein the organotitanium precursor comprises a titanium alkoxide.

20. The method of claim 10, wherein the organic compound-based component is selected from the group consisting of an organic acid or salt thereof, a sugar, a sugar alcohol, and a combination thereof.

21. The method of claim 10, wherein the organic compound-based component is selected from the group consisting of glyoxylic acid, pyruvic acid, lactic acid, malonic acid, oxaloacetic acid, malic acid, fumaric acid, maleic acid, tartaric acid, gluconic acid, citric acid, oxamic acid, serine, aspartic acid, glutamic acid, iminodiacetic acid, ethylenediaminetetraacetic acid, fructose, glucose, galactose, mannose, sucrose, lactose, maltose, erythritol, xylitol, mannitol, sorbitol, and a combination thereof.

22. A method for preparing a bulk catalyst from a bulk catalyst precursor having a formula of

wherein:
  (i) A is an alkali metal cation, a rare earth metal cation, an ammonium cation, an organic ammonium cation, phosphonium cation, or a combination thereof;
  (ii) L is an organic compound-based component; and
  (iii) $0 \leq y \leq -2/p$, $0 \leq x < 2$, $0 \leq v < 2$; $0 < z$; $0 < m < 1$; $0 < n < 4$; $0.1 < w/(z+1) < 10$;
the method comprising:
(a) combining in a reaction mixture:
  (i) a Ni-containing precursor;
  (ii) a Mo-containing precursor;
  (iii) a W-containing precursor;
  (iv) a Ti-containing precursor;
  (v) an organic compound-based component; and
  (vi) a protic liquid; and
(b) reacting the mixture under conditions sufficient to cause precipitation of the bulk catalyst precursor, wherein the steps (a) and (b) are carried out at a temperature of no more than 200° C.;
(c) recovering a bulk catalyst precursor defined by a region of a quaternary phase diagram wherein the region is defined by eight points ABCDEFGH and wherein the eight points, on a metal oxide basis (wt. %), are: A (Ni=52.5, Mo=3.5, W=14, Ti=30), B(Ni=38.5, Mo=17.5, W=14, Ti=30), C(Ni=21, Mo=17.5, W=31.5, Ti=30), D (Ni=35, Mo=3.5, W=31.5, Ti=30), E(Ni=60, Mo=4, W=16, Ti=20), F(Ni=44, Mo=20, W=16, Ti=20), G (Ni=24, Mo=20, W=36, Ti=20), and H (Ni=40, Mo=4, W=36, Ti=20); and
(d) sulfiding the bulk catalyst precursor to form a bulk catalyst.

23. The method of claim 22, wherein the reaction mixture is prepared by:
    preparing a first mixture comprising a Ni-containing precursor, a protic liquid, and, optionally, an organic compound-based component;
    preparing a second mixture comprising a Mo-containing precursor, a W-containing precursor, and a protic liquid;
    adding a Ti-containing precursor to the first mixture, the second mixture, or a combination thereof;
    heating both the first and second mixtures to a temperature of from 60° C. to 150° C.; and
    combining the first and second mixtures together.

24. The method of claim 23, wherein the Ti-containing precursor is selected from TiO$_2$ nanoparticles, colloidal TiO$_2$, fumed TiO$_2$, titanium hydroxide, organotitanium compounds, titanium halides, organotitanium halides, water-soluble titanium salts, or a combination thereof.

25. The method of claim 22, wherein the reacting is carried out at one or more temperatures either (a) in a range of 60° C. to 100° C. under atmospheric pressure or (b) above 100° C. under autogenous pressure.

26. The method of claim 22, wherein the organic compound-based component is selected from an organic acid or salt thereof, a sugar, a sugar alcohol, or a combination thereof.

27. The method of claim 22, wherein the organic compound-based component is selected from glyoxylic acid, pyruvic acid, lactic acid, malonic acid, oxaloacetic acid, malic acid, fumaric acid, maleic acid, tartaric acid, gluconic acid, citric acid, oxamic acid, serine, aspartic acid, glutamic acid, iminodiacetic acid, ethylenediaminetetraacetic acid, fructose, glucose, galactose, mannose, sucrose, lactose, maltose, erythritol, xylitol, mannitol, sorbitol, or a combination thereof.

28. The method of claim 1, further comprising one or more of the following steps:
    compositing the bulk catalyst precursor with 0 to 40 wt. % with a material selected from the group consisting of binder materials, conventional hydroprocessing catalysts, cracking compounds, or mixtures thereof;
    spray-drying, (flash) drying, milling, kneading, slurry-mixing, dry or wet mixing, or combinations thereof;
    shaping, or
    drying and/or thermally treating at a temperature of no more than 200° C.

29. The method of claim 22, wherein the Ti-containing precursor is an organotitanium precursor.

30. The method of claim 29, wherein the organotitanium precursor comprises a titanium alkoxide.

31. A method for preparing a bulk catalyst from a bulk catalyst precursor having a formula of

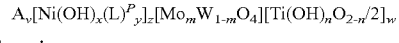

wherein:
  (i) A is an alkali metal cation, a rare earth metal cation, an ammonium cation, an organic ammonium cation, phosphonium cation, or a combination thereof;
  (ii) L is an organic compound-based component; and
  (iii) $0 \leq y \leq -2/p$; $0 \leq x < 2$; $0 \leq v < 2$; $0 < z$; $0 < m < 1$; $0 < n < 4$; $0.1 < w/(z+1) < 10$;

the method comprising:
(a) combining in a reaction mixture:
   (i) a Ni-containing precursor;
   (ii) a Mo-containing precursor;
   (iii) a W-containing precursor;
   (iv) an organic compound-based component; and
   (v) a protic liquid; and
(b) reacting the mixture under conditions sufficient to cause precipitation of an intermediate bulk catalyst precursor; and
(c) compositing the intermediate bulk catalyst precursor with a Ti-containing precursor to form the bulk catalyst precursor;
wherein the steps (a)-(c) are carried out at a temperature of no more than 200° C.; and
(d) recovering a bulk catalyst precursor defined by a region of a quaternary phase diagram wherein the region is defined by eight points ABCDEFGH and wherein the eight points, on a metal oxide basis (wt. %), are: A (Ni=52.5, Mo=3.5, W=14, Ti=30), B(Ni=38.5, Mo=17.5, W=14, Ti=30), C(Ni=21, Mo=17.5, W=31.5, Ti=30), D(Ni=35, Mo=3.5, W=31.5, Ti=30), E(Ni=60, Mo=4, W=16, Ti=20), F(Ni=44, Mo=20, W=16, Ti=20), G (Ni=24, Mo=20, W=36, Ti=20), and H(Ni=40, Mo=4, W=36, Ti=20); and
(e) sulfiding the bulk catalyst precursor to form a bulk catalyst.

32. The method of claim 31, wherein the reaction mixture is prepared by:
preparing a first mixture comprising a Ni-containing precursor, a protic liquid, and, optionally, an organic compound-based component;
preparing a second mixture comprising a Mo-containing precursor, a W-containing precursor, and a protic liquid;
heating both the first and second mixtures to a temperature of from 60° C. to 150° C.; and
combining the first and second mixtures together.

33. The method of claim 31, wherein the Ti-containing precursor is selected from $TiO_2$ nanoparticles, fumed $TiO_2$, or a combination thereof.

34. The method of claim 31, wherein the intermediate bulk catalyst precursor is a Ni—Mo—W bulk catalyst precursor.

35. The method of claim 31, wherein the reacting is carried out at one or more temperatures either (a) in a range of 60° C. to 100° C. under atmospheric pressure or (b) above 100° C. under autogenous pressure.

36. The method of claim 31, wherein the organic compound-based component is selected from an organic acid or salt thereof, a sugar, a sugar alcohol, or a combination thereof.

37. The method of claim 36, wherein the organic compound-based component is selected from glyoxylic acid, pyruvic acid, lactic acid, malonic acid, oxaloacetic acid, malic acid, fumaric acid, maleic acid, tartaric acid, gluconic acid, citric acid, oxamic acid, serine, aspartic acid, glutamic acid, iminodiacetic acid, ethylenediaminetetraacetic acid, fructose, glucose, galactose, mannose, sucrose, lactose, maltose, erythritol, xylitol, mannitol, sorbitol, or a combination thereof.

38. The method of claim 10, further comprising one or more of the following steps:
compositing the bulk catalyst precursor with 0 to 40 wt. % with a material selected from the group consisting of binder materials, conventional hydroprocessing catalysts, cracking compounds, or mixtures thereof;
spray-drying, (flash) drying, milling, kneading, slurry-mixing, dry or wet mixing, or combinations thereof;
shaping, or
drying and/or thermally treating at a temperature of no more than 200° C.

39. The method of claim 31, wherein the Ti-containing precursor is an organotitanium precursor.

40. The method of claim 39, wherein the organotitanium precursor comprises a titanium alkoxide.

* * * * *